(12) United States Patent
Dieterle et al.

(10) Patent No.: US 7,038,080 B2
(45) Date of Patent: May 2, 2006

(54) HETEROGENEOUSLY CATALYZED GAS-PHASE PARTIAL OXIDATION OF ACROLEIN TO ACRYLIC ACID

(75) Inventors: Martin Dieterle, Mannheim (DE); Frieder Borgmeier, Mannheim (DE); Klaus Joachim Mueller-Engel, Stutensee (DE); Hartmut Hibst, Schriesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 181 days.

(21) Appl. No.: 10/667,786

(22) Filed: Sep. 23, 2003

(65) Prior Publication Data

US 2004/0062870 A1   Apr. 1, 2004

(30) Foreign Application Priority Data

| Sep. 27, 2002 | (DE) | ................................ 102 45 585 |
| Oct. 1, 2002 | (DE) | ................................ 102 46 119 |
| Oct. 17, 2002 | (DE) | ................................ 102 48 584 |
| Nov. 20, 2002 | (DE) | ................................ 102 54 278 |
| Nov. 20, 2002 | (DE) | ................................ 102 54 279 |
| Dec. 20, 2002 | (DE) | ................................ 102 61 186 |

(51) Int. Cl.
 *C07C 51/235* (2006.01)
(52) U.S. Cl. .................. 562/535; 562/532; 562/531; 562/523
(58) Field of Classification Search .................... None
 See application file for complete search history.

(56) References Cited

U.S. PATENT DOCUMENTS

| 5,677,261 | A | 10/1997 | Tenten et al. |
| 5,739,391 | A | 4/1998 | Ruppel et al. |
| 5,910,608 | A | 6/1999 | Tenten et al. |
| 6,036,880 | A | 3/2000 | Komada et al. |
| 6,063,728 | A | 5/2000 | Hinago et al. |
| 6,143,916 | A | 11/2000 | Hinago et al. |
| 6,169,214 | B1 | 1/2001 | Tenten et al. |
| 6,407,280 | B1 * | 6/2002 | Chaturvedi et al. ......... 558/319 |
| 6,504,053 | B1 | 1/2003 | Chaturvedi et al. |
| 6,781,008 | B1 * | 8/2004 | Bogan, Jr. .................. 558/323 |
| 6,867,328 | B1 * | 3/2005 | Borgmeier et al. ......... 562/598 |
| 2002/0065431 | A1 | 5/2002 | Chaturvedi et al. |
| 2003/0181762 | A1 | 9/2003 | Machhammer et al. |
| 2003/0187298 | A1 | 10/2003 | Borgmeier et al. |
| 2003/0187299 | A1 | 10/2003 | Machhammer et al. |

FOREIGN PATENT DOCUMENTS

| DE | 198 35 247 | 2/1999 |
| DE | 100 46 672 | 3/2002 |
| DE | 100 51 419 | 4/2002 |
| DE | 101 22 027 | 5/2002 |
| DE | 101 18 814 | 10/2002 |
| DE | 101 19 933 | 10/2002 |
| EP | 0 700 893 | 3/1996 |
| EP | 0 714 700 | 6/1996 |
| EP | 0 938 463 | 9/1999 |
| EP | 1 090 684 | 4/2001 |
| EP | 1 192 987 | 4/2002 |
| JP | 11-343261 | 12/1999 |
| JP | 11-343262 | 12/1999 |
| WO | WO 97/36849 | 10/1997 |
| WO | WO 02/06199 | 1/2002 |

OTHER PUBLICATIONS

Derwent Publications, AN 2000-102178, XP-002270797, JP 11-343261, Dec. 14, 1999.

* cited by examiner

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

A process for the heterogeneously catalyzed gas-phase partial oxidation of acrolein to acrylic acid over a multimetal oxide material having a specific structure, which contains the elements Mo and V, at least one of the elements Te and Sb and at least one of the elements from the group consisting of Nb, Ta, W and Ti and is doped with promoter elements, is described.

27 Claims, 17 Drawing Sheets

HETEROGENEOUSLY CATALYZED GAS-PHASE PARTIAL OXIDATION OF ACROLEIN TO ACRYLIC ACID

The present invention relates to a process for heterogeneously catalyzed gas-phase partial oxidation of acrolein to acrylic acid over a catalytically active multimetal oxide material which contains the elements Mo and V, at least one of the elements Te and Sb and at least one of the elements from the group consisting of Nb, Ta, W and Ti and whose X-ray diffraction pattern has no reflection with the peak position 2θ=50.0±0.3° but has reflections h, i and k whose peaks are at the diffraction angles (2θ) 22.2±0.5° (h), 27.3±0.5° (i) and 28.2±0.5° (k), the reflection h being the strongest one within the X-ray diffraction pattern and having a full width at half height of not more than 0.5°, the intensity $P_i$ of the reflection i and the intensity $P_k$ of the reflection k fulfilling the relationship $0.65 \leq R \leq 0.85$, where R is the intensity ratio defined by the formula $$R = P_i/(P_i + P_k)$$

and the full width at half height of the reflection i and of the reflection k being in each case $\leq 1°$.

Acrylic acid is an important monomer which is used as such or in the form of an alkyl ester for the production of, for example, polymers suitable as adhesives.

Its preparation by heterogeneously catalyzed gas-phase partial oxidation of acrolein to acrylic acid is generally known (cf. for example EP-A 714700 or EP-A 700893, and the literature cited in these publications) and is important in particular as the second oxidation stage in the preparation of acrylic acid by two-stage heterogeneously catalyzed gas-phase partial oxidation starting from propene.

The process evaluated in the preamble is disclosed in DE-A 10119933 and in DE-A 10118814. In these two publications, the X-ray diffraction pattern according to the preamble of this document is assigned to a phase which is referred to both in the two publications and in this document as an i-phase. Similar processes are disclosed in EP-A 1090684, in JP-A 11/343261, in JP-A 11/343262 and in EP-A 938463.

A disadvantage of the processes of the prior art is that the selectivity of the acrylic acid formation is not completely satisfactory.

It is an object of the present invention to provide an improved process for the preparation of acrylic acid, which process starts from acrolein and has, inter alia, high selectivity to the acrylic acid formation. It was known from EP-A 1192987 that, with the use of multimetal oxide materials according to the preamble of this document as active materials for the one-stage preparation of acrylic acid by heterogeneously catalyzed gas-phase partial oxidation of propane or of propane and propene, an improvement in the process can be achieved by doping the multimetal oxide materials with at least one element from the group consisting of Ni, Pd, Cu, Ag and Au.

We have found that this object is achieved by a process for the heterogeneously catalyzed gas-phase partial oxidation of acrolein to acrylic acid over a catalytically active multimetal oxide material which contains the elements Mo and V, at least one of the elements Te and Sb and at least one of the elements from the group consisting of Nb, Ta, W and Ti and whose X-ray diffraction pattern has no reflection with the peak position 2θ=50.0±0.3° but has reflections h, i and k whose peaks are at the diffraction angles (2θ) 22.2±0.5° (h), 27.3±0.5° (i) and 28.2±0.5° (k), the reflection h being the strongest one within the X-ray diffraction pattern and having a full width at half height of not more than 0.5°, the intensity $P_i$ of the reflection i and the intensity $P_k$ of the reflection k fulfilling the relationship $0.65 \leq R \leq 0.85$, where R is the intensity ratio defined by the formula $$R = P_i/(P_i + P_k)$$

and the full width at half height of the reflection i and of the reflection k is in each case $\leq 1°$, wherein the catalytically active multimetal oxide material is one of the stoichiometry I

$$Mo_1V_aM^1{}_bM^2{}_cM^3{}_dO_n \qquad (I),$$

where $M^1$ is at least one of the elements from the group consisting of Te and Sb;

$M^2$ is at least one of the elements from the group consisting of Nb, Ti, W, Ta and Ce;

$M^3$ is at least one of the elements from the group consisting of Pb, Ni, Co, Bi, Pd, Ag, Pt, Cu, Au, Ga, Zn, Sn, In, Re, Ir, Sm, Sc, Y, Pr, Nd and Tb;

a=from 0.01 to 1, b=from >0 to 1, c=from 0.1 to 1, d=from >0 to 0.5 and n is a number which is determined by the valency and frequency of the elements other than oxygen in (I).

Figure 1:
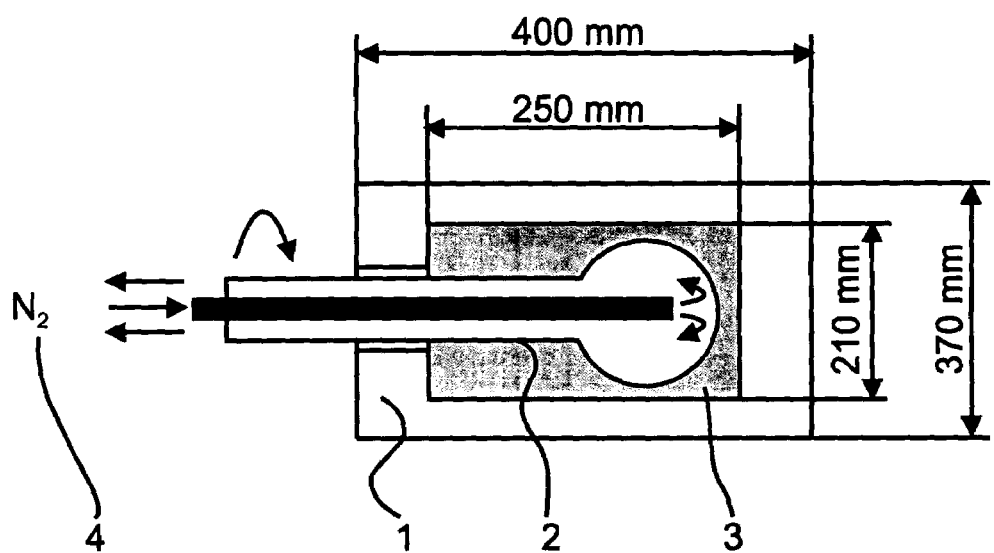
FIG. 1 Schematic of the rotating bulb furnace

All data in this document which relate to an X-ray diffraction pattern are based on an X-ray diffraction pattern produced using CuKα radiation (Siemens diffractometer Theta-Theta D-5000, tube voltage: 40 kv, tube current: 40 mA, aperture V20 (variable), collimator aperture V20 (variable), secondary monochromator aperture (0.1 mm), detector aperture (0.6 mm), measuring interval (2θ):0.02°, measuring time per step: 2.4 s, detector: scintillation counter; the definition of the intensity of a reflection in the X-ray diffraction pattern is based in this document on the definition stated in DE-A 19835247, DE-A 10122027, DE-A 10051419 and DE-A 10046672; the same applies to the definition of the full width at half height).

According to the invention, preferably $0.67 \leq R \leq 0.75$ and very particularly preferably R=from 0.69 to 0.75 or R=from 0.71 to 0.74 or R=0.72.

In addition to the reflections h, i and k, the X-ray diffraction pattern of multimetal oxide materials (I) to be used according to the invention contains, as a rule, further reflections whose peaks are at the following diffraction angles (2θ):

9.0±0.40 (l),
6.7±0.40 (o) and
7.9±0.40 (p).

According to the invention, it is furthermore advantageous if the X-ray diffraction pattern additionally contains a reflection whose peak is at the diffraction angle (2θ)=45.2±0.4° (q).

Frequently, the X-ray diffraction pattern of multimetal oxide materials (I) to be used according to the invention also contains the reflections 29.2±0.4° (m) and 35.4±0.4° (n) (peak positions).

If the intensity 100 is assigned to the reflection h, it is advantageous according to the invention if the reflections i, l, m, n, o, p and q have the following intensities on the same intensity scale:

i: from 5 to 95, frequently from 5 to 80, in some cases from 10 to 60;
l: from 1 to 30;
m: from 1 to 40;
n: from 1 to 40;
o: from 1 to 30;
p: from 1 to 30 and
q: from 5 to 60.

If the X-ray diffraction pattern of the multimetal oxide materials (I) to be used according to the invention contains additional reflections from among the abovementioned ones, the full width at half height thereof is as a rule $\leq 1°$.

The specific surface area of multimetal oxide materials (I) to be used according to the invention is in many cases from 1 to 40, often from 11 or 12 to 40, frequently from 15 or 20 to 40 or 30, m²/g (determined by the BET method, nitrogen).

It is preferred according to the invention if the stoichiometric coefficient a of the multimetal oxide materials (I) to be used according to the invention is from 0.05 to 0.6, particularly preferably from 0.1 to 0.6 or 0.5, independently of the preferred ranges of the other stoichiometric coefficients.

Independently of the preferred ranges of the other stoichiometric coefficients of the multimetal oxide materials (I) to be used according to the invention, the stoichiometric coefficient b is preferably from 0.01 to 1, particularly preferably from 0.01 or 0.1 to 0.5 or 0.4.

The stoichiometric coefficient c of the multimetal oxide materials (I) to be used according to the invention is from 0.01 to 1, particularly preferably from 0.01 or 0.1 to 0.5 or 0.4, independently of the preferred ranges of the other stoichiometric coefficients of the multimetal oxide materials (I). A range for the stoichiometric coefficient c which is very particularly preferred according to the invention and which, independently of the preferred ranges for the other stoichiometric coefficients of multimetal oxide materials (I) to be used according to the invention, can be combined with all other preferred ranges in this document is the range from 0.05 to 0.2.

It is preferred according to the invention that the stoichiometric coefficient d of the multimetal oxide materials (I) to be used according to the invention is from 0.00005 or 0.0005 to 0.5, particularly preferably from 0.001 to 0.5, frequently from 0.002 to 0.3, often from 0.005 or 0.01 to 0.1, independently of the preferred ranges for the other stoichiometric coefficients of the multimetal oxide materials (I).

Particularly advantageous multimetal oxide materials (I) to be used according to the invention are those whose stoichiometric coefficients a, b, c and d are simultaneously in the following ranges:

a=from 0.05 to 0.6;
b=from 0.01 to 1 (or from 0.01 to 0.5);
c=from 0.01 to 1 (or from 0.01 to 0.5); and
d=from 0.0005 to 0.5 (or from 0.001 to 0.3).

Very particularly advantageous multimetal oxide materials (I) to be used according to the invention are those whose stoichiometric coefficients a, b, c and d are simultaneously in the following ranges:

a=from 0.1 to 0.6;
b=from 0.1 to 0.5;
c=from 0.1 to 0.5; and
d=from 0.001 to 0.5 or from 0.002 to 0.3 or from 0.005 to 0.1.

$M^1$ is preferably Te.

All of the abovementioned applies in particular when at least 50 mol % of $M^2$, based on its total amount, comprises Nb and very particularly preferably when 75 mol % of $M^2$, based on its total amount or 100 mol % of $M^2$, based on its total amount, is Nb.

However, it also applies in particular, regardless of the meaning of $M^2$, when $M^3$ is at least one element from the group consisting of Ni, Co, Bi, Pd, Ag, Au, Pb and Ga or at least one element from the group consisting of Ni, Co, Pd and Bi.

However, all of the abovementioned also applies in particular when at least 50 or at least 75 or 100 mol % of $M^2$, based on its total amount, is Nb and $M^3$ is at least one element from the group consisting of Ni, Co, Bi, Pd, Ag, Au, Pb and Ga.

However, all of the abovementioned also applies in particular when at least 50 or at least 75 or 100 mol % of $M^2$, based on its total amount, is Nb and $M^3$ is at least one element from the group consisting of Ni, Co, Pd and Bi.

Very particularly preferably, all statements regarding the stoichiometric coefficients apply when $M^1$ is Te, $M^2$ is Nb and $M^3$ is at least one element from the group consisting of Ni, Co and Pd.

The principle of a targeted process for the preparation of multimetal oxide materials (I) to be used according to the invention is disclosed, for example, in WO 0206199 and the literature references cited in this document. According to these, a multimetal oxide material which has the stoichiometry (I) but is generally an intimately intergrown solid solution system comprising i-phase and other phases (e.g. k-phase) is first produced in a manner known per se. According to DE-A 10119933 and DE-A 10118814, for example, a typical feature of the k-phase is the X-ray diffraction pattern has reflections of the strongest intensity at the 2θ peak positions 22.1±0.3°, 28.2±0.3°, 36.2±0.3°, 45.2±0.3° and 50.0±0.3°. The i-phase fraction can then be isolated from this solid solution by washing out the other phases, for example k-phase, with suitable liquids. Suitable such liquids are, for example, organic acids and aqueous solutions of organic acids (e.g. oxalic acid, formic acid, acetic acid, citric acid and tartaric acid), inorganic acids (e.g. nitric acid), aqueous solutions of inorganic acids (e.g. aqueous telluric acid or aqueous nitric acid), alcohols and aqueous hydrogen peroxide solutions. Furthermore, JP-A 7-232071 also discloses a process for the preparation of i-phase multimetal oxide materials. The washing process of EP-A 1254707 is also suitable.

Solid solution systems comprising i- and k-phase are obtained, as a rule, by the preparation processes described in the prior art (cf. for example DE-A 19835247, EP-A 529853, EP-A 603836, EP-A 608838, EP-A 895809, DE-A 19835247, EP-A 962253, EP-A 1080784, EP-A 1090684, EP-A 1123738, EP-A 1192987, EP-A 1192986, EP-A 1192982, EP-A 1192983 and EP-A 1192988). In these processes, a very intimate, preferably finely divided, dry blend is produced from suitable sources of the elemental constituents of the multimetal oxide materials and said dry blend is thermally treated at from 350 to 700° C. or from 400 to 650° C. or from 400 to 600° C. The thermal treatment can be effected in principle under either an oxidizing, reducing or inert atmosphere. A suitable oxidizing atmosphere is, for example, air, air enriched with molecular oxygen or air depleted in oxygen. However, the thermal treatment is preferably carried out under an inert atmosphere, i.e. for example under molecular nitrogen and/or noble gas. Usually, the thermal treatment is effected at atmospheric pressure (1 atm). Of course, the thermal treatment can also be effected under reduced or superatmospheric pressure.

If the thermal treatment is effected under a gaseous atmosphere, this may be either stationary or flowing. It is preferably flowing. Altogether, the thermal treatment may take up to 24 hours or more.

The thermal treatment is preferably effected initially under an oxidizing (oxygen-containing) atmosphere (e.g. under air) at from 150 to 400° C. or from 250 to 350° C. (=preliminary decomposition step). The thermal treatment is then expediently continued under an inert gas at from 350 to 700° C. or from 400 to 650° C. or from 450 to 600° C. Of course, the thermal treatment can also be effected in such a way that the catalyst precursor material, before its thermal treatment, is first (if required after pulverization) pelleted (with or without addition of from 0.5 to 2% by weight of finely divided graphite), then thermally treated and subsequently converted into chips again.

The thorough mixing of the starting compounds can be effected in dry or in wet form.

If it is effected in dry form, the starting compounds are expediently used in the form of finely divided powder and, after mixing and any compaction, are subjected to calcining (thermal treatment).

However, the thorough mixing is preferably effected in wet form. Usually, the starting compounds are mixed with one another in the form of an aqueous solution (if required, in the presence of complexing agents; cf. for example DE-A 10145958) and/or suspension. Thereafter, the aqueous material is dried and then calcined. The aqueous material is expediently an aqueous solution or an aqueous suspension. The drying process is preferably effected immediately after the preparation of the aqueous mixture (particularly in the case of an aqueous solution; cf. for example JP-A 7-315842) and by spray-drying (the exit temperatures are as a rule from 100 to 150° C.; the spray-drying can be carried out by the cocurrent or countercurrent method), which requires a particularly intimate dry blend, especially when the aqueous material to be spray-dried is an aqueous solution or suspension. However, drying may also be effected by evaporation under reduced pressure, by freeze-drying or by conventional evaporation.

Suitable sources of the elemental constituents for carrying out the above-described preparation method for i-/k-phase solid solution multimetal oxide materials are all those which are capable of forming oxides and/or hydroxides on heating (if necessary in air). Of course, the actual oxides and/or hydroxides of the elemental constituents may also be concomitantly used or exclusively used as such starting compounds, i.e. all starting compounds stated in EP-A 1254707, EP-A 1254709 and EP-A 1192987 are particularly suitable.

Suitable sources of the element Mo are, for example, molybdenum oxides, such as molybdenum trioxide, molybdates, such as ammonium heptamolybdate tetrahydrate, and molybdenum halides, such as molybdenum chloride.

Suitable starting compounds for the element V are, for example, vanadium oxysulfate hydrate, vanadyl acetylacetonate, vanadates, such as ammonium metavanadate, vanadium oxides, such as vanadium pentoxide ($V_2O_5$), vanadium halides, such as vanadium tetrachloride($VCl_4$), and vanadium oxyhalides, such as $VOCl_3$. Other vanadium starting compounds which may also be present are those which contain the vanadium in the oxidation state +4.

Suitable sources of the element tellurium are tellurium oxides, such as tellurium dioxide, metallic tellurium, tellurium halides, such as $TeCl_2$, and telluric acids, such as orthotelluric acid $H_6TeO_6$.

Advantageous antimony starting compounds are antimony halides, such as $SbCl_3$, antimony oxides, such as antimony trioxide ($Sb_2O_3$), antimonic acids, such as $HSb(OH)_6$, and antimony oxide salts, such as antimony oxide sulfate $(SbO)_2SO_4$ and antimony acetate.

Suitable niobium sources are, for example, niobium oxides, such as niobium pentoxide ($Nb_2O_5$), niobium oxyhalides, such as $NbOCl_3$, niobium halides, such as $NbCl_5$, and complex compounds of niobium and organic carboxylic acids and/or dicarboxylic acid, e.g. oxalates and alcoholates. Of course, the Nb-containing solutions used in EP-A 895 809 are also suitable as a niobium source.

Regarding all other possible elements (in particular Pb, Ni, Cu, Co, Bi and Pd), particularly suitable starting compounds are their halides, nitrates, formates, oxalates, acetates, carbonates and/or hydroxides. Suitable starting compounds are often also their oxo compounds, e.g. tungstates, or the acids derived from these. Ammonium salts are also frequently used as starting compounds.

Furthermore, polyanions of the Anderson type, as described, for example, in Polyhedron 6, No. 2 (1987), 213–218, are also suitable as starting compounds. A further suitable literature source for polyanions of the Anderson type is Kinetics and Catalysis, 40, No. 3 (1999), 401 to 404.

Other polyanions suitable as starting compounds are, for example, those of the Dawson or Keggin type. Preferably used starting compounds are those which are converted into their oxides at elevated temperatures either in the presence or in the absence of oxygen, with or without liberation of gaseous compounds.

i-/k-phase solid solution multimetal oxide materials obtainable as described (pure i-phase multimetal oxide may be accidentally obtained by the procedure described) can then be converted in the manner described by suitable washing (in which as a rule the stoichiometry changes only insignificantly) into multimetal oxides (I) to be used according to the invention. After the washing, calcination is preferably effected again, as described in EP-A 1254709.

The calcination conditions are as a rule the same as those also recommended for the preparation of the multimetal oxide material to be washed.

An increased proportion of the i-phase (and in advantageous cases substantially pure i-phase) is established in the preparation of the precursor multimetal oxides (which can be converted by washing described into novel multimetal oxides (I)) when their preparation is carried out by a hydrothermal method, as described, for example, in DE-A 10029338, DE-A 10254278 and JP-A 2000-143244. In this case, too, recalcination can be effected in accordance with EP-A 1254709.

The preparation of multimetal oxide materials (I) to be used according to the invention can, however, also be effected by first producing a multimetal oxide material I' which differs from a multimetal oxide material (I) only in that d is 0.

Such a preferred finely divided multimetal oxide material I' can then be impregnated with solutions (e.g. aqueous ones) of elements $M^3$ (e.g. by spraying), subsequently dried (preferably at $\leq 100°$ C.) and then calcined (preferably in an inert gas stream) as described above for the precursor multimetal oxides (here, preliminary decomposition in air is preferably dispensed with). The use of aqueous nitrate and/or halide solutions of elements $M^3$ and/or the use of aqueous solutions in which the elements $M^3$ are present in a form of complexed with organic compounds (e.g. acetates or acetylacetonates) are particularly advantageous for this preparation variant.

The multimetal oxides (I) obtainable in the manner described and to be used according to the invention can be used as such [e.g. as powder or after pelleting of the powder (frequently with addition of from 0.5 to 2% by weight of finely divided graphite) and subsequent comminution to give chips] or can be shaped into moldings for the novel process. The catalyst bed may be a fixed bed, a moving bed or a fluidized bed.

The shaping to give moldings can be effected, for example, by application to a support, as described in DE-A 10118814 or PCT/EP/02/04073 or DE-A 10051419. It is also possible to proceed according to DE-A 4442346.

The supports to be used for the multimetal oxide materials (I) used in the novel process are preferably chemically inert, i.e. they do not substantially intervene in the course of the novel partial catalytic gas-phase oxidation which is catalyzed by the multimetal oxide materials (I) to be used according to the invention.

According to the invention, suitable materials of the supports is in particular alumina, silica, silicates, such as clay, kaolin, steatite (preferably having a low water-soluble alkali content and preferably from Ceramtec in Germany), pumice, aluminum silicate and magnesium silicate, silicon carbide, zirconium dioxide and thorium dioxide.

The surface of the support may be either smooth or rough. Advantageously, the surface of the support is rough since a high degree of surface roughness generally results in greater adhesion to the applied coat of active material.

Frequently, the surface roughness Rz of the support is from 5 to 200 μm, often from 20 to 100 μm (determined according to DIN 4768, Sheet 1, using a Hommel tester for DIN-ISO surface parameters from Hommelwerke, Germany).

Furthermore, the support material may be porous or nonporous. The support material is expediently nonporous (total volume of the pores, based on the volume of the support, $\leq 1\%$ by volume).

The thickness of the coat of active oxide material present on the novel coated catalyst is usually from 10 to 1 000 μm.
However, it may also be from 50 to 700 μm, from 100 to 600 μm or from 150 to 400 μm. Possible coat thicknesses are also from 10 to 500 μm, from 100 to 500 μm or from 150 to 300 mm.

In principle, any desired geometries of the supports are suitable for the novel process. Their longest dimension is as a rule from 1 to 10 mm. However, spheres or cylinders, in particular hollow cylinders, are preferably used as supports. Advantageous diameters for spherical supports are from 1.5 to 5 mm. If cylinders are used as supports, their length is preferably from 2 to 10 mm and their external diameter is preferably from 4 to 10 mm. In the case of rings, the wall thickness is moreover usually from 1 to 4 mm. Annular supports suitable according to the invention may also have a length of from 3 to 6 mm, an external diameter of from 4 to 8 mm and a wall thickness of from 1 to 2 mm. However, a support ring geometry of 7 mm×3 mm×4 mm or of 5 mm×3 mm×2 mm (external diameter×length×internal diameter) is also possible.

Coated catalysts to be used according to the invention can be prepared in a very simple manner, for example by preforming multimetal oxide materials of the formula (I) which are to be used according to the invention, converting them into a finely divided form and finally applying them to the surface of the support with the aid of a liquid binder. For this purpose, the surface of the support is moistened in a very simple manner and, by bringing it into contact with finely divided active oxide material of the formula (I), a coat of the active material is caused to adhere to the moistened surface. Finally, the coated support is dried. Of course, the process can be periodically repeated in order to obtain a greater coat thickness. In this case, the coated parent body becomes the new support, etc. After coating is complete, calcination can be effected again under the abovementioned conditions (preferably once again under inert gas, for example washed multimetal oxide (I)).

The fineness of the catalytically active multimetal oxide material of the formula (I) which is to be applied to the surface of the support is of course adapted to the desired coat thickness. For the coat thickness range of from 100 to 500 μm, for example, active material powder of which at least 50% of the total number of powder particles pass through a sieve of mesh size from 1 to 20 μm and whose numerical proportion of particles having the longest dimension above 50 μm is less than 10% are suitable. As a result of the preparation, the distribution of the longest dimensions of the powder particles corresponds as a rule to a Gaussian distribution. Frequently, the particle size distribution is as follows:

| D (μm) | 1 | 1.5 | 2 | 3 | 4 | 6 | 8 | 12 |
|---|---|---|---|---|---|---|---|---|
| x | 80.5 | 76.3 | 67.1 | 53.4 | 41.6 | 31.7 | 23 | 13.1 |
| y | 19.5 | 23.7 | 32.9 | 46.6 | 58.4 | 68.3 | 77 | 86.9 |
| D (μm) | 16 | 24 | 32 | 48 | 64 | 96 | 128 | |
| x | 10.8 | 7.7 | 4 | 2.1 | 2 | 0 | 0 | |
| y | 89.2 | 92.3 | 96 | 97.9 | 98 | 100 | 100 | |

Here:
D = diameter of the particle,
x = percentage of particles whose diameter is $\geq$ D; and
y = percentage of particles whose diameter is <D.

For example, the use of the basic process disclosed in DE-A 2909671 and of that disclosed in DE-A 10051419 is advisable for carrying out the coating process described on an industrial scale, i.e. the supports to be coated are initially taken in a preferably inclined (the angle of inclination is as a rule $\geq 0°$ and $\leq 90°$, in general $\geq 30°$ and $\leq 90°$; the angle of inclination is the angle of the central axis of the rotating container relative to the horizontal) rotating container (e.g. rotating pan or coating drum). The rotating container transports the supports, for example spherical or cylindrical ones, under two metering apparatuses arranged in succession a certain distance apart. The first of the two metering apparatuses expediently corresponds to a nozzle (for example an atomizer nozzle operated with compressed air) through which the supports rolling in the rotating pan are sprayed with the liquid binder and moistened in a controlled manner. The second metering apparatus is located outside the atomization cone of the liquid binder sprayed in and serves for feeding in the finely divided active oxide material (e.g. via a vibrating chute or a powder screw). The spherical supports moistened in a controlled manner take up the active material powder fed in, which becomes compacted to a cohesive coat by the rolling movement on the outer surface of the support, for example the cylindrical spherical support.

If required, the support provided in this manner with a base coat once again passes through the spray nozzles in the course of the subsequent revolution, is moistened in a controlled manner in order to be able to take up a further coat of finely divided active oxide material in the course of the further movement, etc. (intermediate drying is as a rule not necessary). Finely divided active oxide material and liquid binder are as a rule fed in continuously and simultaneously.

The liquid binder can be removed after the end of the coating, for example by the action of hot gases, such as $N_2$ or air. It is noteworthy that the coating process described produces both completely satisfactory adhesion of the successive coats to one another and of the base coat to the surface of the support.

What is important for the coating procedure described above is that the moistening of the support surface to be coated is carried out in a controlled manner. In short, this means that the support surface is expediently moistened so that, although it adsorbs liquid binder, no liquid phase as such is visible on the support surface. If the support surface is too moist, the finely divided catalytically active oxide material agglomerates to form separate agglomerates instead of adhering to the surface.

Detailed information in this context is to be found in DE-A 2909671 and in DE-A 10051419.

The abovementioned final removal of the liquid binder used can be carried out in a controlled manner, for example by evaporation and/or sublimation. In the simplest case, this can be effected by the action of hot gases of appropriate temperature (frequently from 50 to 300° C., often 150° C.). However, it is also possible to effect only preliminary drying by the action of hot gases. The final drying can then be carried out, for example, in a drying oven of any type (e.g. belt dryer) or in the reactor. The prevailing temperature should not be above the calcination temperature used for the preparation of the active oxide material. Of course, the drying can also be carried out exclusively in a drying oven.

Regardless of the type and of the geometry of the support, the following may be used as a binder for the coating process: water, monohydric alcohols, such as ethanol, methanol, propanol and butanol, polyhydric alcohols, such as ethylene glycol, 1,4-butanediol, 1,6-hexanediol or glycerol, monobasic or polybasic organic carboxylic acids, such as propionic acid, oxalic acid, malonic acid, glutaric acid or maleic acid, amino alcohols, such as ethanolamine or diethanolamine, and monofunctional or polyfunctional organic amides, such as formamide. Advantageous binders are also solutions consisting of from 20 to 90% by weight of water and from 10 to 80% by weight of an organic compound which is dissolved in water and whose boiling point or sublimation temperature at atmospheric pressure (1 atm) is >100° C., preferably >150° C. Advantageously, the organic compound is selected from the above list of possible organic binders. The organic content of abovementioned aqueous binder solutions is preferably from 10 to 50, particularly preferably from 20 to 30, % by weight. Other suitable organic components are monosaccharides and oligosaccharides, such as glucose, fructose, sucrose or lactose, and polyethylene oxides and polyacrylates.

What is important is that the preparation of coated catalysts suitable according to the invention can be effected not only by applying the prepared, finely milled active oxide materials of the formula (I) to the moistened support surface.

Rather, instead of the active oxide material, is it also possible to apply a finely divided precursor material thereof to the moistened support surface (with the use of the same coating process and binder) and to carry out the calcination after drying of the coated support (it is also possible for supports to be impregnated with a precursor solution, subsequently dried and then calcined). Finally, the phases other than the i-phase can, if required, be washed out. Calcination can then be effected again in the manner described.

A suitable finely divided precursor material of this type is, for example, the material which is obtainable by producing, from the sources of the elemental constituents of the desired active oxide material of the formula (I) which is to be used according to the invention, a very intimate, preferably finely divided, dry blend (for example by spray-drying of an aqueous suspension or solution of the sources) and subjecting this finely divided dry blend (if required, after pelleting with the addition of from 0.5 to 2% by weight of finely divided graphite) to a thermal treatment (for a few hours) at from 150 to 350° C., preferably from 250 to 350° C., under an oxidizing (oxygen-containing) atmosphere (e.g. under air) and, if required, finally subjecting it to milling.

After the coating of the supports with the precursor material, calcination is then effected, preferably under an inert gas atmosphere (all other atmospheres are also suitable) at from 360 to 700° C. or from 400 to 650° C. or from 400 to 600° C.

Of course, the shaping of multimetal oxide materials (I) which can be used according to the invention can also be effected by extrusion and/or pelleting of both finely divided multimetal oxide material (I) and finely divided precursor material of a multimetal oxide material (I) (if required, the washing out of the phases other than the i-phase can be effected finally, if required including a recalcination).

Suitable geometries are spheres, solid cylinders and hollow cylinders (rings). The longest dimension of the abovementioned geometries is as a rule from 1 to 10 mm. In the case of cylinders, their length is preferably from 2 to 10 mm and their external diameter preferably from 4 to 10 mm. In the case of rings, the wall thickness is moreover usually from 1 to 4 mm. Unsupported annular catalysts suitable according to the invention may also have a length of from 3 to 6 mm, an external diameter of from 4 to 8 mm and a wall thickness of from 1 to 2 mm. However, an unsupported annular catalyst geometry of 7 mm×3 mm×4 mm or of 5 mm×3 mm×2 mm (external diameter×length×internal diameter) is also possible.

For the novel process, all those geometries in DE-A 10101695 are of course also suitable for the geometry of the multimetal oxide active materials (I) to be used.

As stated above, what is important according to the invention is that the multimetal oxide materials (I) to be used according to the invention have an X-ray diffraction pattern (in this document, always based on CuK$_\alpha$ radiation) which has reflections h, i and k whose peaks are at the diffraction angles (2θ) 22.2±0.4°(h), 27.3±0.4°(i) and 28.2±0.4°(k), the reflection h being the one with the strongest intensity within the X-ray diffraction pattern and having a full width at half height of not more than 0.5°, the intensity $P_i$ of the reflection i and the intensity $P_k$ of the reflection k fulfilling the relationship 0.65≦R≦0.85, where R is the intensity ratio defined by the formula $$R = P_i/(P_i + P_k)$$

and the full width at half height of the reflection i and of the reflection k being in each case ≦1°.

At the same time, the X-ray diffraction pattern should have no reflection with a peak position 2θ=50.0±0.3°.

In this document, as stated above, the definition of the intensity of a reflection in the X-ray diffraction pattern is based on the definition given in DE-A 19835247 and that given in DE-A 10051419 and DE-A 10046672.

This means that, if $A^1$ is the peak of a reflection 1 and if $B^1$ is the next pronounced minimum (reflection shoulders having minima are not taken into account) to the left of the peak $A^1$ in the line of the X-ray diffraction pattern when viewed along the intensity axis perpendicular to the 2θ axis, and, in a corresponding manner, $B^2$ is the nearest pronounced minimum to the right of the peak $A^1$ and if $C^1$ is the point at which a straight line drawn from the peak $A^1$ perpendicular to the 2θ axis intersects a straight line connecting the points $B^1$ and $B^2$, then the intensity of the reflection 1 is the length of the straight line segment $A^1C^1$ which extends from the peak $A^1$ to the point $C^1$. Here, the expression minimum means a point at which the gradient of a tangent to the curve in a base region of the reflection 1 changes from a negative value to a positive value, or a point at which the gradient tends to zero, the coordinates of the 2θ axis and of the intensity axis being used for determining the gradient.

In this document, the full width at half height is in a corresponding manner the length of the straight line segment which results between the two points of intersection $H^1$ and $H^2$ if a line parallel to the 2θ axis is drawn in the middle of the straight line segment $A^1C^1$, $H^1$ and $H^2$ being the respective first point of intersection of this parallel line with the above-defined line of the X-ray diffraction pattern to the left and right of $A^1$.

Figure 6:
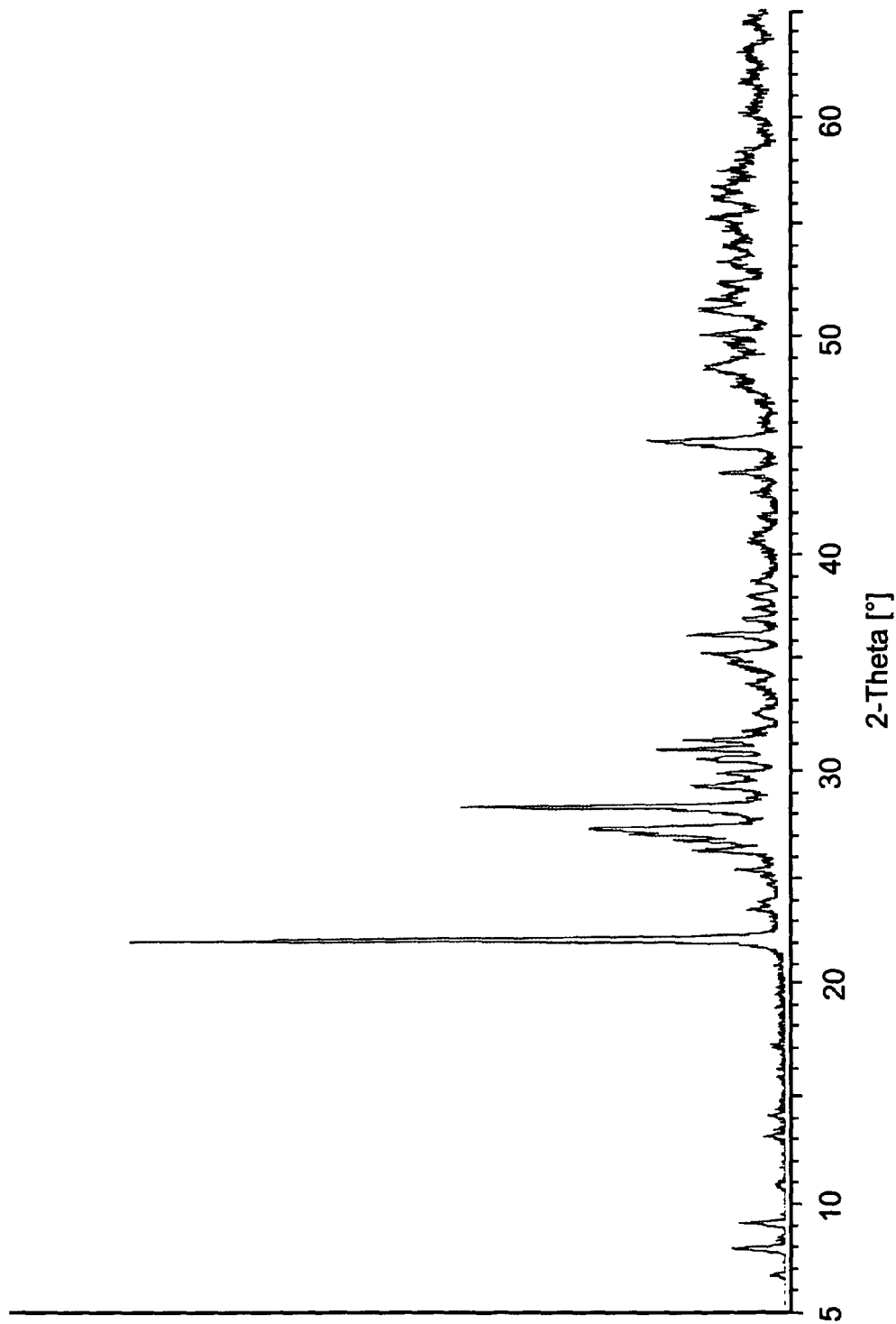
FIG. 6 X-ray diffraction pattern of Comparative Example 3

An exemplary procedure for determining the full width at half height and the intensity is also shown in FIG. 6 in DE-A 10046672.

Of course, the multimetal oxide materials (I) to be used according to the invention can also be used as catalytically active materials in a form diluted with finely divided, e.g. colloidal, materials, such as silica, titanium dioxide, alumina, zirconium oxide or niobium oxide.

The dilution mass ratio may be up to 9 (diluent):1 (active material), i.e. possible dilution ratios are, for example, 6 (diluent):1 (active material and 3 (diluent):1 (active material. The incorporation of the diluent can be effected before and/or after the calcination, as a rule even before the drying.

Usually, it is effected before the shaping.

If the incorporation is effected before the drying or before the calcination, the diluent must be chosen so that it is substantially retained in the fluid medium or during the calcination. This generally occurs, for example, in the case of oxides calcined at appropriately high temperatures.

Moreover, the novel process for the heterogeneously catalyzed gas-phase partial oxidation of acrolein to acrylic acid can be carried out as described in EP-A 714700 or in EP-A 700893 and the literature cited in these publications, i.e. usually a reaction gas starting mixture which comprises acrolein, molecular oxygen and at least one inert gas comprising at least 20%, based on its volume, of molecular nitrogen and which contains the molecular oxygen and the acrolein in a molar $O_2:C_3H_4O$ ratio of ≧1 is passed at elevated temperatures over or through a catalyst bed (as a rule a fixed bed) whose active material is a multimetal oxide material (I) in such a way that the acrolein conversion in a single pass is ≧90 mol % and the associated selectivity of the acrylic acid formation is ≧90 mol %.

Expediently, the novel process is used as the second oxidation stage in the preparation of acrylic acid by two-stage catalytic gas-phase oxidation starting from propene. The reaction gas starting mixture used here is usually the product gas mixture of the first oxidation stage, if required supplemented by a source of molecular oxygen.

The suitable source for the molecular oxygen required in the novel process is air or air depleted in molecular nitrogen (e.g. ≧90% by volume of $O_2$≦10% by volume of $N_2$).

As stated above, the molar $O_2$:acrolein ratio in the reaction gas starting mixture is preferably ≧1 in the novel process. Usually, this ratio is ≦3. According to the invention, the molar $O_2$:acrolein ratio in the reaction gas starting mixture is frequently from 1 to 2 or from 1 to 1.5.

In the novel process, the operating pressure may be either below atmospheric pressure (e.g. up to 0.5 bar) or above atmospheric pressure. Typically, the operating pressure is from 1 to 5, preferably from 1 to 3, bar. Usually, the reaction pressure does not exceed 100 bar.

In the novel process, the acrolein content of the reaction gas starting mixture may be from 3 to 15% by volume, frequently from 4 to 10 or from 5 to 8% by volume (based in each case on the total volume).

The novel process is frequently carried out at an acrolein: oxygen:steam:inert gas volume ratio (l(S.T.P.) of 1:(1 to 3):(0 to 20):(3 to 30), preferably of 1:(1 to 3):(0.5 to 10):(7 to 8).

The reaction temperature for the novel process is typically from 220 to 300° C., frequently from 230 to 280° C.

The space velocity of a fixed catalyst bed in the novel process may be ≧100 l(S.T.P.) of acrolein per l of catalyst per h, but in general ≦300 l(S.T.P.) of acrolein per l of catalyst per h.

Preferably used inert diluent gases in the novel process are those which undergo a conversion of less than 5, preferably less than 2, mol % in a single pass.

Inert diluent gases suitable according to the invention are in particular $CO_2$, CO, $N_2$, noble gases and steam.

It is advantageous to carry out the novel process in the presence of propane and/or propene. This is because the novel catalysts are also capable of catalyzing their partial oxidation to acrylic acid.

Of course, the novel process can also be carried out as a high-load process in more than one reaction zone, as described, for example, in DE-A 19910508, DE-A 19948248 and DE-A 19927624.

The novel process is carried out in the presence of propane and/or propene inter alia when it is the third reaction stage of a three-stage preparation of acrylic acid from propane, as described, for example, in EP-A 938463, DE-A 19837518, DE-A 19837518, DE-A 19837517, DE-A 19837520, DE-A 10246119 and DE-A 10245585 and the literature cited in these publications.

Moreover, it is advantageous in the novel process to change the composition of the reaction gas starting mixture at least once analogously to DE-A 10122027 while carrying out the process so that the amount of the diluent gas steam contained in the reaction gas starting mixture, based on the molar amount of acrolein contained in the reaction gas starting mixture, before the change is lower after the change.

Of course, the novel process gives a product mixture which does not consist exclusively of acrylic acid. Rather, in addition to unconverted acrolein, the product gas mixture contains secondary components, such as propene, propane, $CO_2$, CO, $H_2O$, acetic acid, propionic acid, etc., from which the acrylic acid has to be separated off.

This can be carried out as in DE-A 10122027. The residual gas remaining in this separation can be further used as recycle gas (recycling as a rule into a propene and/or propane oxidation) or can be incinerated and used, for example, for the generation of steam and/or for energy production.

Multimetal oxide materials (I) deactivated during the novel process can be reactivated by passing over gases containing molecular oxygen and/or steam, under the temperature and pressure conditions of the reaction causing the deactivation. Such a gas may be, for example, air, a mixture of air and steam or lean air (air depleted in molecular oxygen) or a mixture of steam and lean air. It is also possible to use a mixture of nitrogen and steam.

The oxygen content of the regeneration gas can accordingly be from $\geq 0$ to 20 mol %. It is frequently from 2 to 10, sometimes from 2 to 15, mol %.

Moreover, the conditions of EP-A 1090684, of JP-A 11/343262 and of JP-A 11/343261 can also be used for the novel process.

The multimetal oxide materials (I) to be used according to the invention can, however, also be integrated into other multimetal oxide materials and used for the novel process (for example, those recommended in DE-A 19910508 as multimetal oxide active materials for the heterogeneously catalyzed gas-phase partial oxidation of acrolein to acrylic acid; for example, by mixing their finely divided materials, if required molding them and calcining them, or by mixing them as (preferably aqueous) slurries, drying them and calcining them. Once again, calcination is preferably effected under inert gas. The calcination temperature used is usually one which has been used for the preparation of the multimetal oxide materials to be integrated in one another. Usually, the lowest calcination temperatures are used. In advantageous cases, it is also possible to dispense with the calcination after the mixing.

The resulting multimetal oxide materials (referred to below as total materials) contain preferably $\geq 50$, particularly preferably $\geq 75$, very particularly preferably >90 or $\geq 95$, % by weight of the multimetal oxide materials (I) to be used according to the invention.

The total materials preferably also have no reflection peak position at $2\theta=50.0\pm0.3°$. If the total amount has a reflection peak position at $2\theta=50.0\pm0.3°$, it is advantageous if the amount by weight of the novel multimetal oxide materials (I) is $\geq 80\%$ by weight or $\geq 90\%$ by weight or $\geq 95\%$ by weight. Such total materials may also contain multimetal oxides of the stoichiometry (I) in the k-phase structure and are obtainable, for example, if washing out is not effected quantitatively in the preparation of multimetal oxide materials (I) to be used according to the invention. R is preferably $\geq 0.65$ and $\geq 0.90$ for the total materials.

In the case of the total materials, the geometrical shaping is expediently effected as described for the multimetal oxide materials (I).

The advantageousness of the multimetal oxide materials (I) used according to the invention is based on their excellent selectivity with respect to the desired product. It is surprising hat the promoters $M^3$ in the pure i-phase are effective for the novel process.

According to the invention, the process for the heterogeneously catalyzed gas-phase partial oxidation of acrolein to acrylic acid is preferably carried out in a tube-bundle reactor, advantageously in such a way that the volume-specific activity of the catalyst load increases continuously and/or abruptly in the direction of flow of reaction gas mixture, as practiced, for example, in the working example based in a comparable active material in DE-A 10246119.

Finally, it should be stated that the novel process can also be carried out in such a way that a reaction gas starting mixture substantially free of molecular oxygen is passed at elevated temperatures over the multimetal oxide material, the spent multimetal oxide material is then reoxidized with a gas containing molecular oxygen (e.g. air), reaction gas starting mixture substantially free of molecular oxygen is then again passed over, etc. The abovementioned procedure is preferably carried out in a fluidized bed. As a rule, it results in a further improvement in the selectivity.

EXAMPLES

A) Preparation of Coated Catalysts Comprising Multimetal Oxide Materials

Comparative example 1 (preparation of a multimetal oxide catalyst having the active material $Mo_{1.0}V_{0.33}Te_{0.19}Nb_{0.11}Ni_{0.01}O_x$, comprising i- and k-phases)

87.61 g of ammonium metavanadate (78.55% by weight of $V_2O_5$, from G. f. E. Nürnbern, Germany) were dissolved at 80° C. in 3 040 ml of water (three-necked flask having a stirrer, thermometer, reflux condenser and heating) while stirring. A clear, yellowish solution formed. This solution was cooled to 60° C., and then 117.03 g of telluric acid (99% by weight of $H_6TeO_6$, from Aldrich) and 400.00 g of ammonium heptamolybdate (82.52% by weight of $MoO_3$, from Starck/Goslar) was stirred in succession in said sequence into the solution while maintaining the 60° C. The resulting deep red solutions cooled to 30° C., and then 25.60 g of an aqueous solution of 6.80 g of nickel(II) nitrate hexahydrate (98% by weight, from Fluka) in 20 g of water (dissolution was effected at 25° C.) were added while maintaining the 30° C. A solution A which was at 30° C. was thus obtained.

Separately therefrom, 112.67 g of ammonium niobium oxalate (20.8% by weight of Nb, from Starck/Goslar) were dissolved at 60° C. in 500 ml of water in a beaker to give a solution B. Solution B was cooled to 30° C. and was combined at this temperature with a solution A which was at the same temperature, the solution B being added to solution A. The addition was effected continuously over a period of 5 minutes. An orange suspension formed.

This suspension was then spray-dried in a spray dryer from Niro (spray dryer Niro A/S Atomizer, Transportable Minor unit, centrifugal atomizer from Niro, Denmark). The temperature of the initially taken mixture was 30° C. The gas entry temperature $T^{in}$ was 320° C. and the gas exit temperature $T^{out}$ was 110° C. The resulting spray-dried powder was likewise orange.

100 g of the spray-dried powder were heated in a rotating bulb furnace according to FIG. 1 (quartz glass bulb having an internal volume of 1 liter; 1=furnace housing, 2=rotating bulb, 3=heated space, 4=nitrogen/air stream) under an air stream of 50 l(S.T.P.)/h in the course of 27.5 minutes, initially linearly from 25° C. to 275° C., and this temperature and the air stream were then maintained for 1 hour. Immediately thereafter, the air stream was replaced by a nitrogen stream of 50 l(S.T.P.)/h and heating was effected linearly from 275° C. to 600° C. in the course of 32.5 minutes. This temperature and the nitrogen stream were then maintained for 2 hours. Finally, while maintaining the nitrogen stream, the entire rotating bulb furnace was cooled to 25° C.

Figure 2:
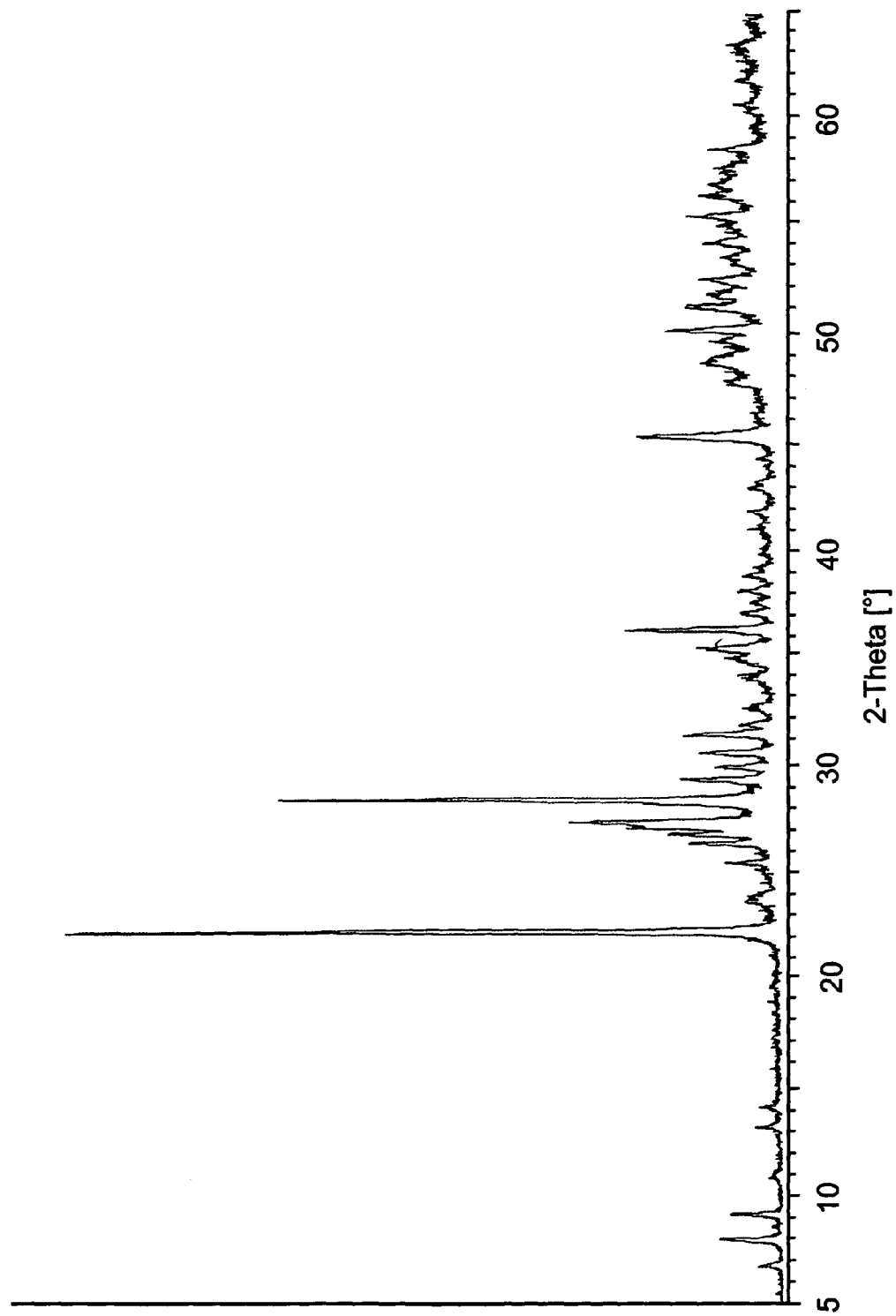
FIG. 2 X-ray diffraction pattern of Comparative Example 1

A black powder having the composition $Mo_{1.0}V_{0.33}Te_{0.19}Nb_{0.11}Ni_{0.01}O_x$ (stoichiometry of weighed-in sample: $Mo_{1.0}V_{0.33}Te_{0.22}Nb_{0.11}Ni_{0.01}O_x$) was obtained. The associated X-ray diffraction pattern is shown in FIG. 2 (R=0.26). BET=8.0 m$^2$/g.

The active material powder was then milled in a Retsch mill (centrifugal mill, type ZM 100, from Retsch, Germany) (particle size $\leq$0.12 mm).

38 g of the powder present after milling were applied to 150 g of spherical supports having a diameter of from 2.2 to 3.2 mm ($R_z$=45 µm, support material=steatite from Ceramtec, Germany, total pore volume of the support $\leq$1% by volume, based on the total support volume). For this purpose, the support was introduced into a coating drum having an internal volume of 2 l (angle of inclination of the central axis of the drum relative to the horizontal=30°). The drum was rotated at 25 revolutions per minute. About 25 ml of a mixture of glycerol and water (glycerol:water weight ratio=1:3) was sprayed onto the support over 60 minutes via an atomizer nozzle operated with 300 l(S.T.P.)/h of compressed air. The nozzle was installed in such a way that the spray cone wet the supports transported in the drum by driver plates to the uppermost point of the inclined drum, in the upper half of the rolling zone. The finely divided active material powder was introduced into the drum via a powder screw, to the point of addition of the powder being within the rolling zone or below the spray cone. By periodic repetition of wetting and powder metering, the support provided with a base coat itself became the support in the subsequent period.

After the end of the coating, the coated support was dried under air for 16 hours at 150° C. in a muffle furnace. A coated catalyst VB1 comprising 20% by weight of active material resulted.

Example 1

As in comparative example 1. The powder resulting after the milling in the Retsch mill was, however, stirred in 1 000 ml of a 10% strength by weight HNO$_3$ solution for 7 hours at 70° C. under reflux. The remaining solid was filtered off from the resulting slurry and was washed nitrate-free with water. The filter cake was then dried overnight under air at 110° C. in a muffle furnace.

Figure 3:
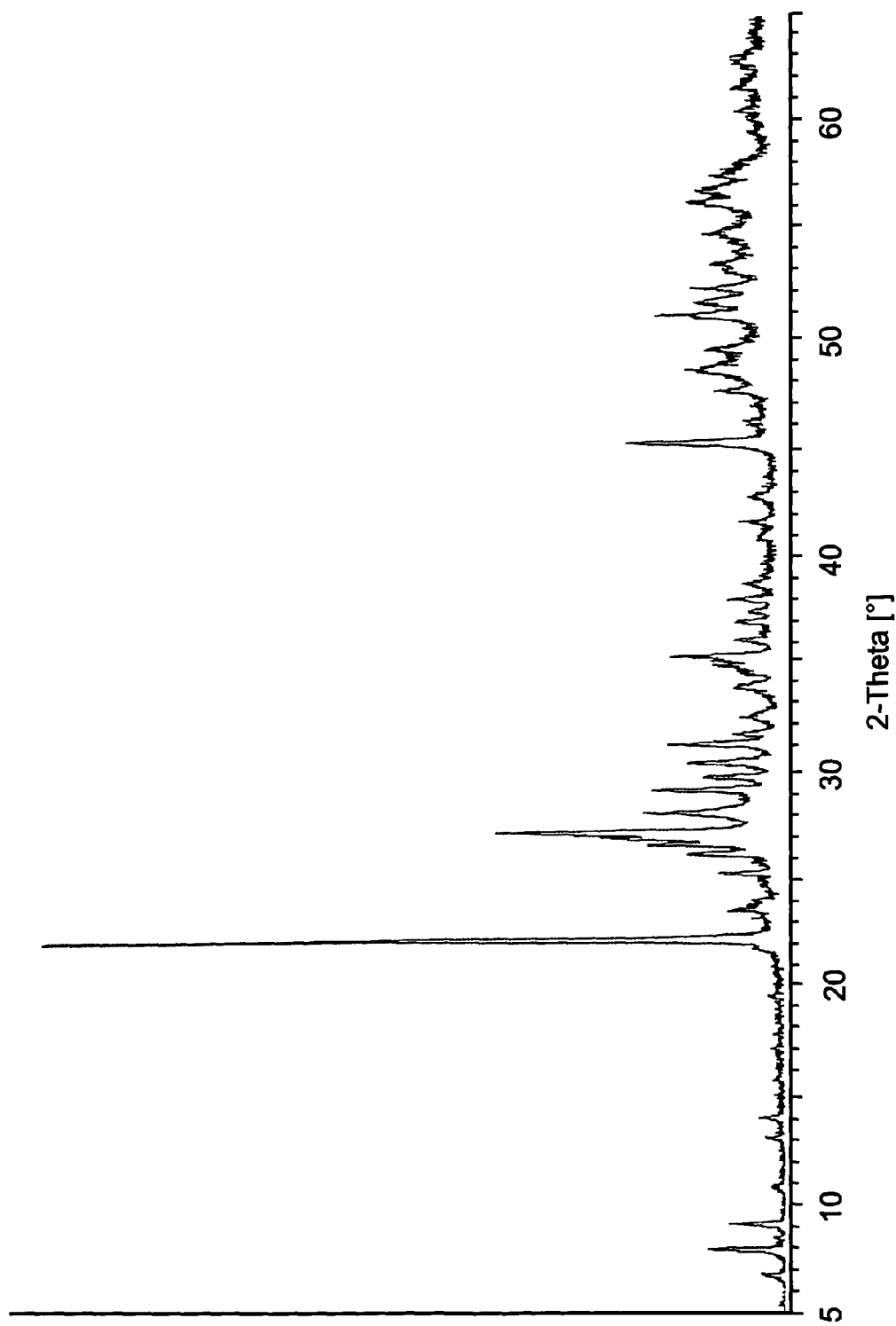
FIG. 3 X-ray diffraction pattern of Example 1

The resulting active material had the composition $Mo_{1.0}V_{0.29}Te_{0.14}Nb_{0.13}Ni_{0.007}O_x$. The associated X-ray diffraction pattern is shown in FIG. 3 (R=0.71). BET=20.2 m$^2$/g.

It was applied in the same manner to the same support as in comparative example 1, so that a coated catalyst VB1 comprising 20% by weight of active material resulted.

Comparative Example 2

As in comparative example 1, but 6.17 g of palladium(II) nitrate dihydrate (98%, from Fluka) were used instead of 6.80 g of nickel(II) nitrate hexahydrate.

Figure 4:
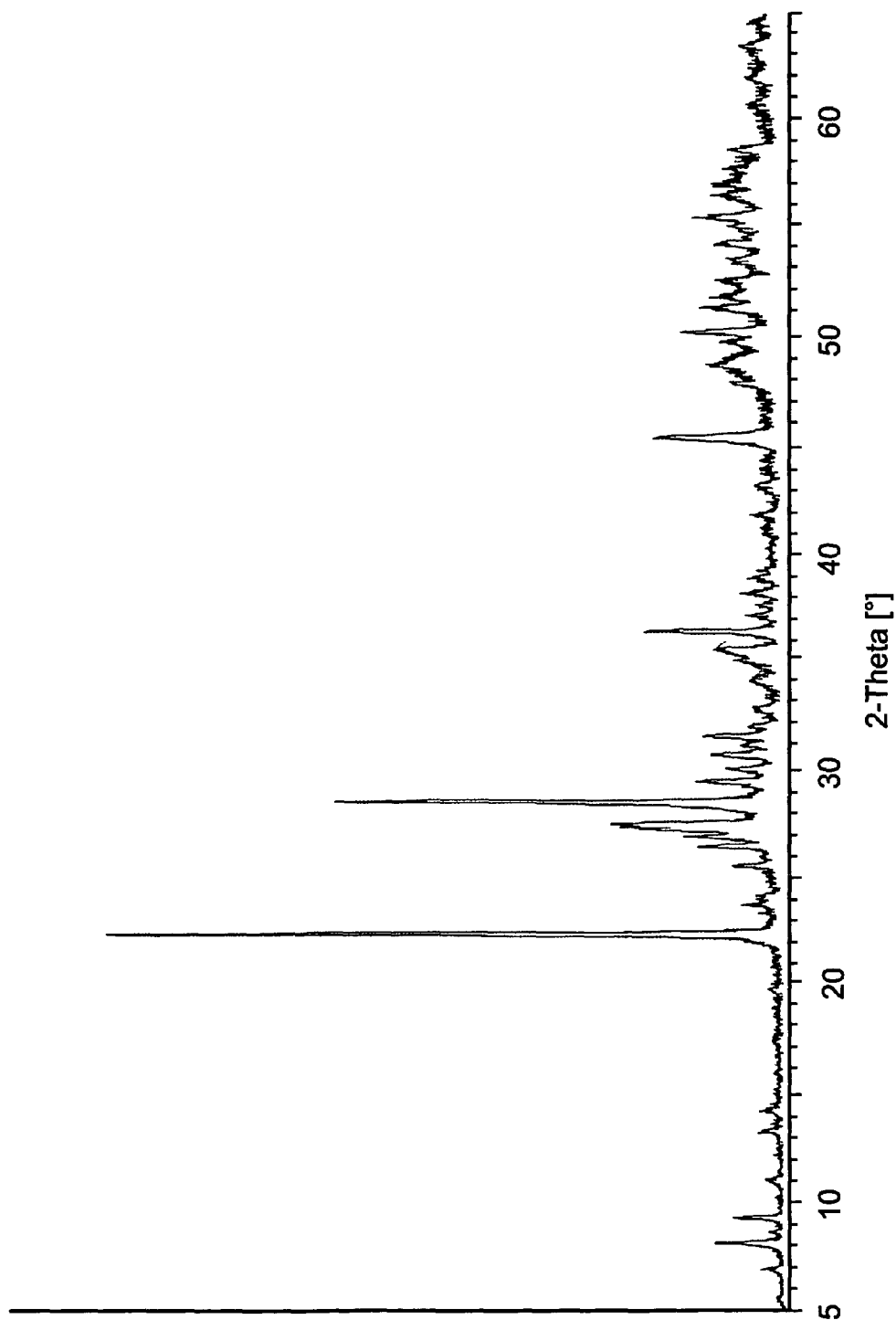
FIG. 4 X-ray diffraction pattern of Comparative Example 2

The resulting active material had the composition $Mo_{1.0}V_{0.33}Te_{0.19}Nb_{0.11}Pd_{0.01}O_x$. The associated X-ray diffraction pattern is shown in FIG. 4 (R=0.25). BET=9.3 m$^2$/g. It was applied in the same manner to the same support as in comparative example 1, so that a coated catalyst VB2 comprising 20% by eight of active material resulted.

Example 2

As in example 1, but the active material from comparative example 2 was washed with aqueous nitric acid. The resulting active material had the composition $Mo_{1.0}V_{0.28}Te_{0.13}Nb_{0.13}Pd_{0.001}O_x$.

Figure 5:
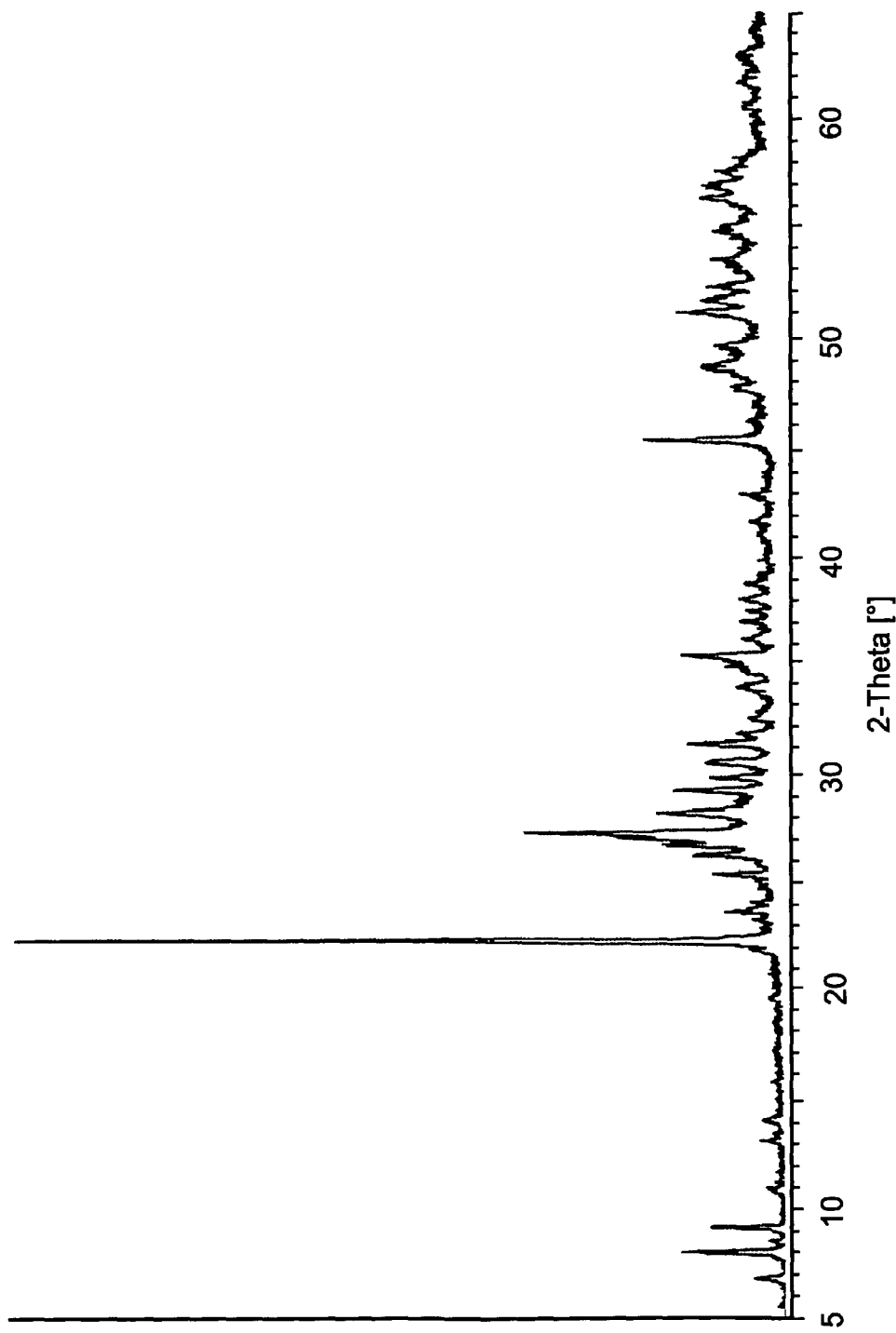
FIG. 5 X-ray diffraction pattern of Example 2

The associated X-ray diffraction pattern is shown in FIG. 5 (R=0.73). BET=22.5 m$^2$/g. It was applied in the same manner to the same support as in comparative example 1, so that a coated catalyst B2 comprising 20% by weight of active material resulted.

Comparative Example 3

As in comparative example 1, but half the amount of the batch was used in the procedure and then, instead of 3.40 g of nickel(II) nitrate hexahydrate, 12.34 g of palladium(II) nitrate dihydrate (98%, from Fluka) were used.

The resulting active material had the composition $Mo_{1.0}V_{0.33}Te_{0.22}Nb_{0.11}Pd_{0.04}O_x$. The associated X-ray diffraction pattern is shown in FIG. 6 (R=0.35). BET=9.3 m$^2$/g. It was applied in the same manner to the same support as in comparative example 1, so that a coated catalyst VB3 comprising 20% by weight of active material resulted.

Example 3

Figure 7:
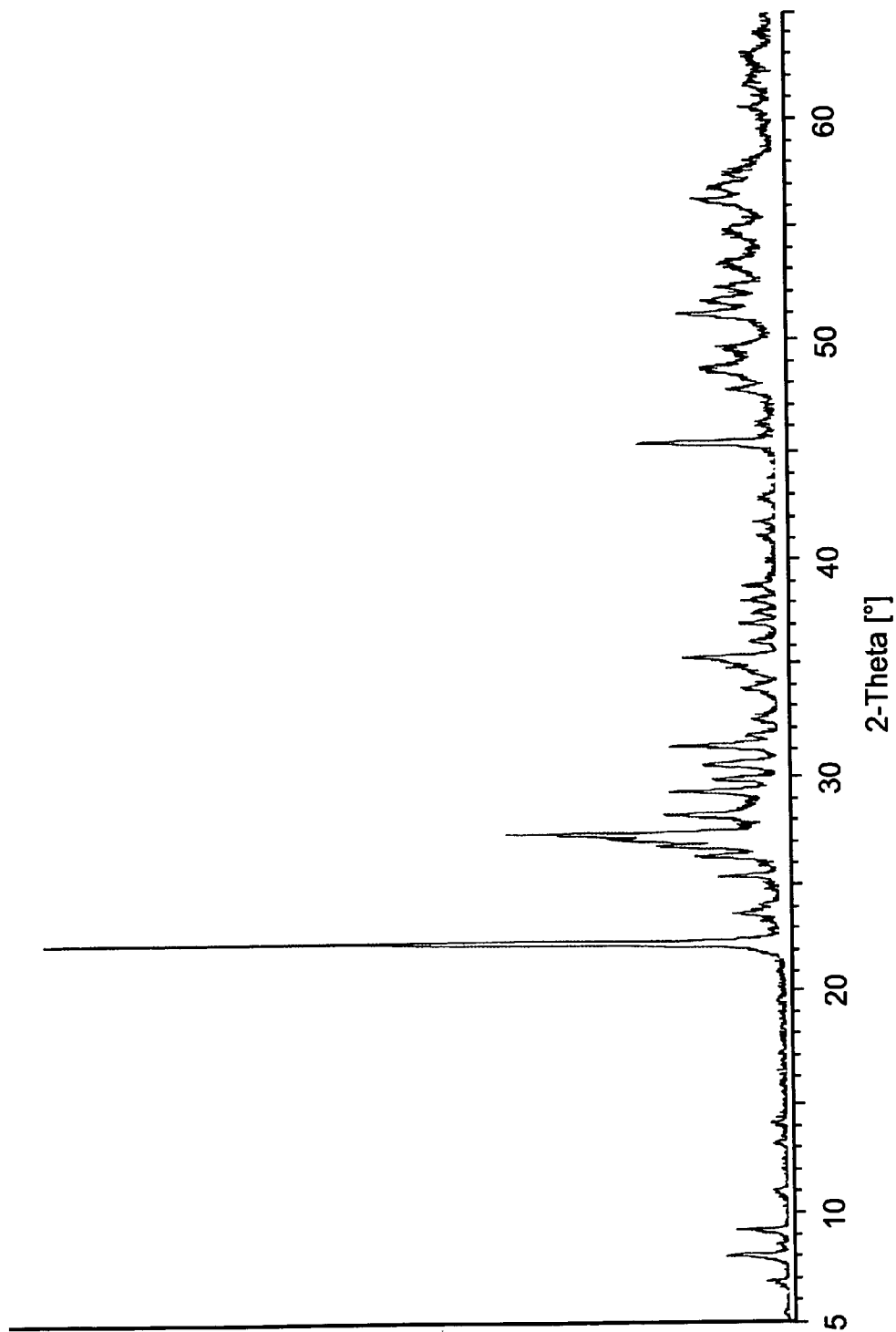
FIG. 7 X-ray diffraction pattern of Example 3

As in example 1, but the active material from comparative example 3 was washed with aqueous nitric acid. The resulting active material had the composition $Mo_{1.0}V_{0.29}Te_{0.13}Nb_{0.13}Pd_{0.001}O_x$. The associated X-ray diffraction pattern is shown in FIG. 7 (R=0.74). BET=17.4 m$^2$/g. It was applied in the same manner to the same support as in comparative example 1, so that a coated catalyst B3 comprising 20% by weight of active material resulted.

Comparative Example 4

As in comparative example 1, but 3.41 g of cobalt(II) nitrate hexahydrate (98%, from Riedel-de-Haen) were used instead of 6.80 g of nickel(II) nitrate hexahydrate.

Figure 8:
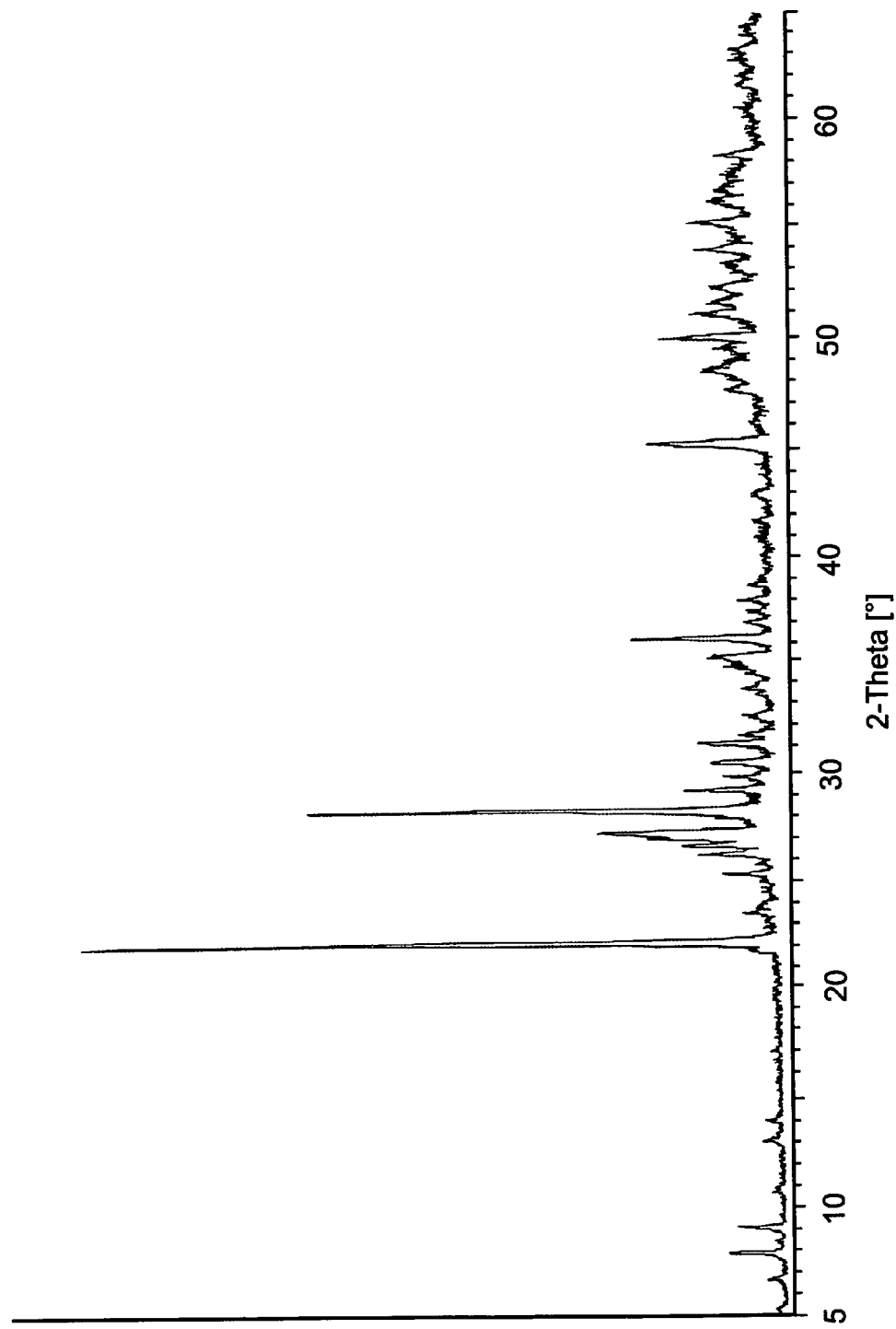
FIG. 8 X-ray diffraction pattern of Comparative Example 4

The resulting active material had the composition $Mo_{1.0}V_{0.33}Te_{0.19}Nb_{0.11}Co_{0.005}O_x$. The associated X-ray diffraction pattern is shown in FIG. 8 (R=0.24). BET=8.9 m$^2$/g. It was applied in the same manner to the same support as in comparative example 1, so that a coated catalyst VB4 comprising 20% by weight of active material resulted.

Example 4

As in example 1, but the active material from comparative example 4 was washed with aqueous nitric acid.

Figure 9:
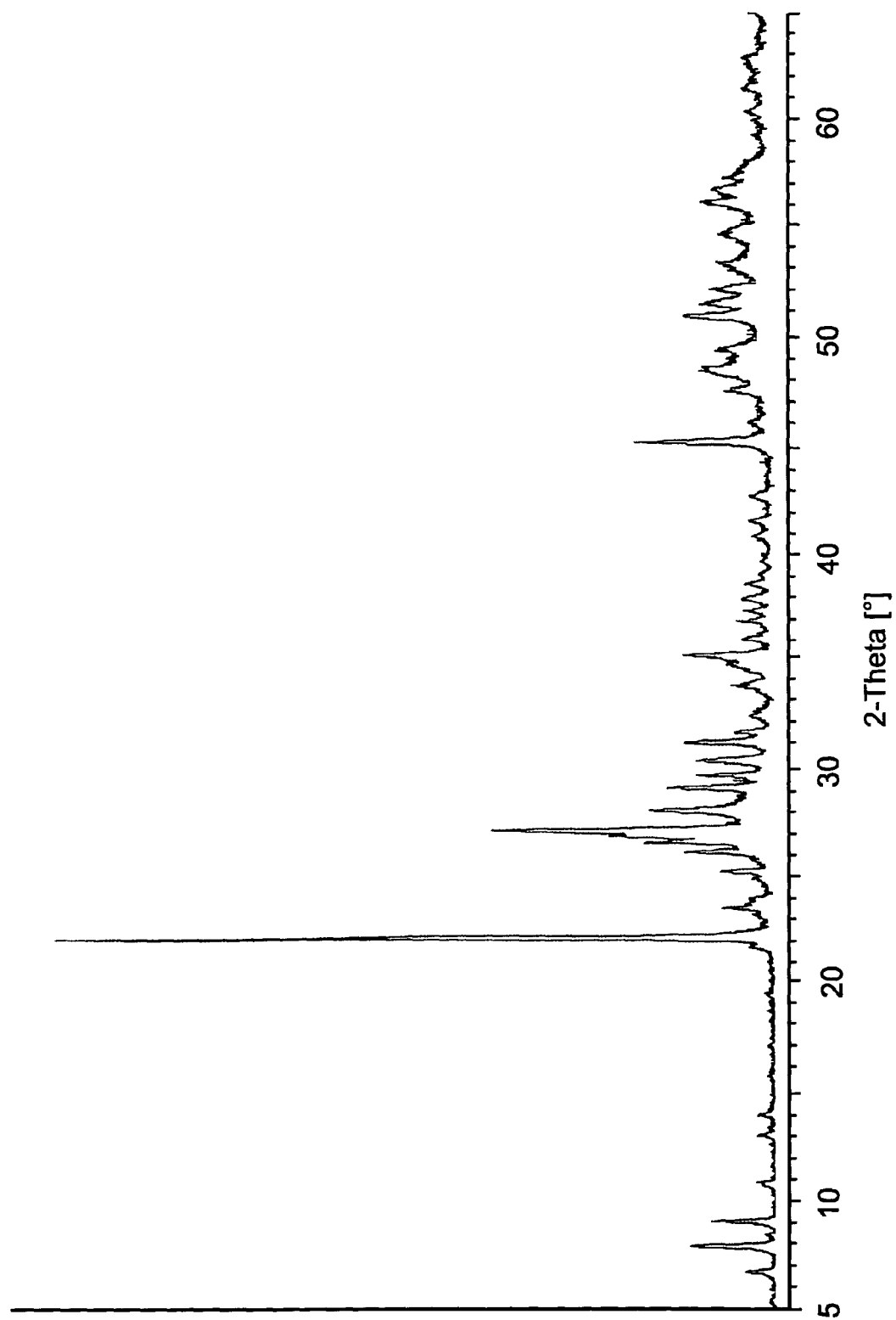
FIG. 9 X-ray diffraction pattern of Example 4

The resulting active material had the composition $Mo_{1.0}V_{0.29}Te_{0.13}Nb_{0.13}Co_{0.004}O_x$. The associated X-ray diffraction pattern is shown in FIG. 9 (R=0.73). BET=24.6 m²/g. It was applied in the same manner to the same support as in comparative example 1, so that a coated catalyst B4 comprising 20% by weight of active material resulted.

Comparative Example 5

As in comparative example 1, but 5.65 g of copper(II) nitrate trihydrate (99%, from Acros organics) were used instead of 6.80 g of nickel(II) nitrate hexahydrate.

Figure 10:
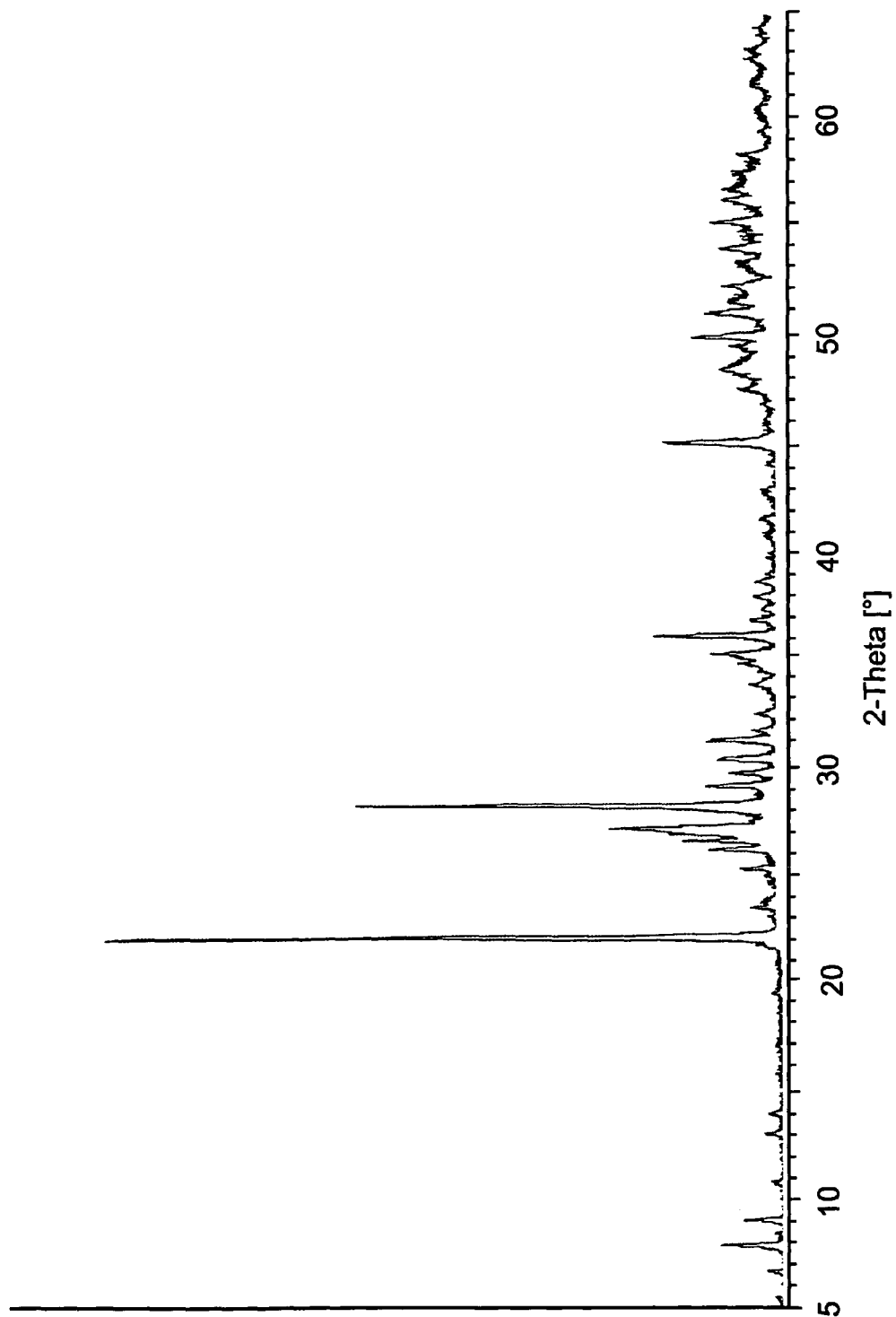
FIG. 10 X-ray diffraction pattern of Comparative Example 5

The resulting active material had the composition $Mo_{1.0}V_{0.33}Te_{0.19}Nb_{0.11}Co_{0.01}O_x$. The associated X-ray diffraction pattern is shown in FIG. 10 (R=0.27). BET=6.7 m²/g. It was applied in the same manner to the same support as in comparative example 1, so that a coated catalyst VB5 comprising 20% by weight of active material resulted.

Example 5

As in example 1, but the active material from comparative example 5 was washed with aqueous nitric acid.

Figure 11:
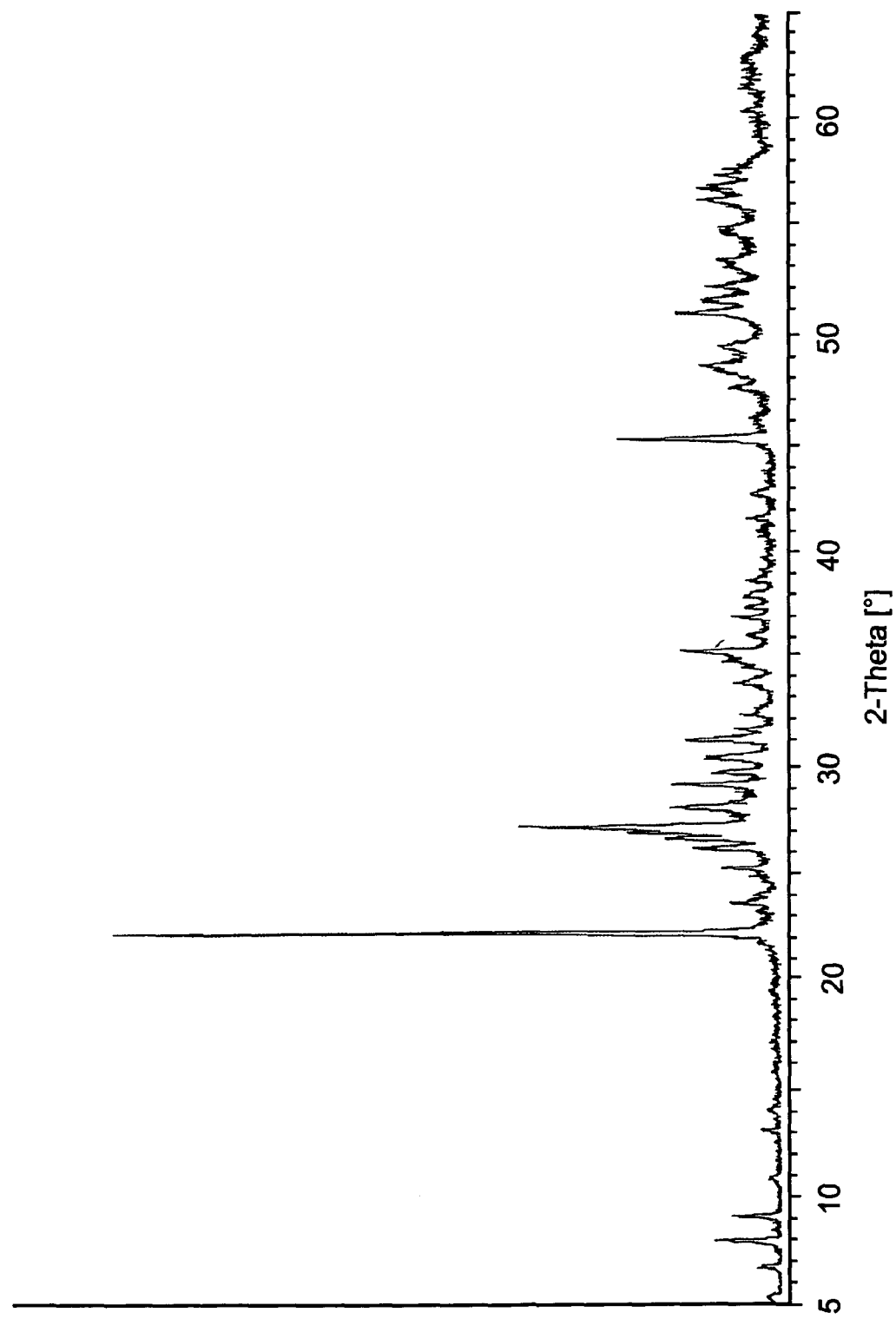
FIG. 11 X-ray diffraction pattern of Example 5

The resulting active material had the composition $Mo_{1.0}V_{0.28}Te_{0.13}Nb_{0.13}Cu_{0.003}O_x$. The associated X-ray diffraction pattern is shown in FIG. 11 (R=0.74). BET=23.1 m²/g. It was applied in the same manner to the same support as in comparative example 1, so that a coated catalyst B5 comprising 20% by weight of active material resulted.

Comparative Example 6

As in comparative example 1, but 5.68 g of bismuth(III) nitrate pentahydrate (98.5%, from Merck) were used instead of 6.80 g of nickel(II) nitrate hexahydrate.

Figure 12:
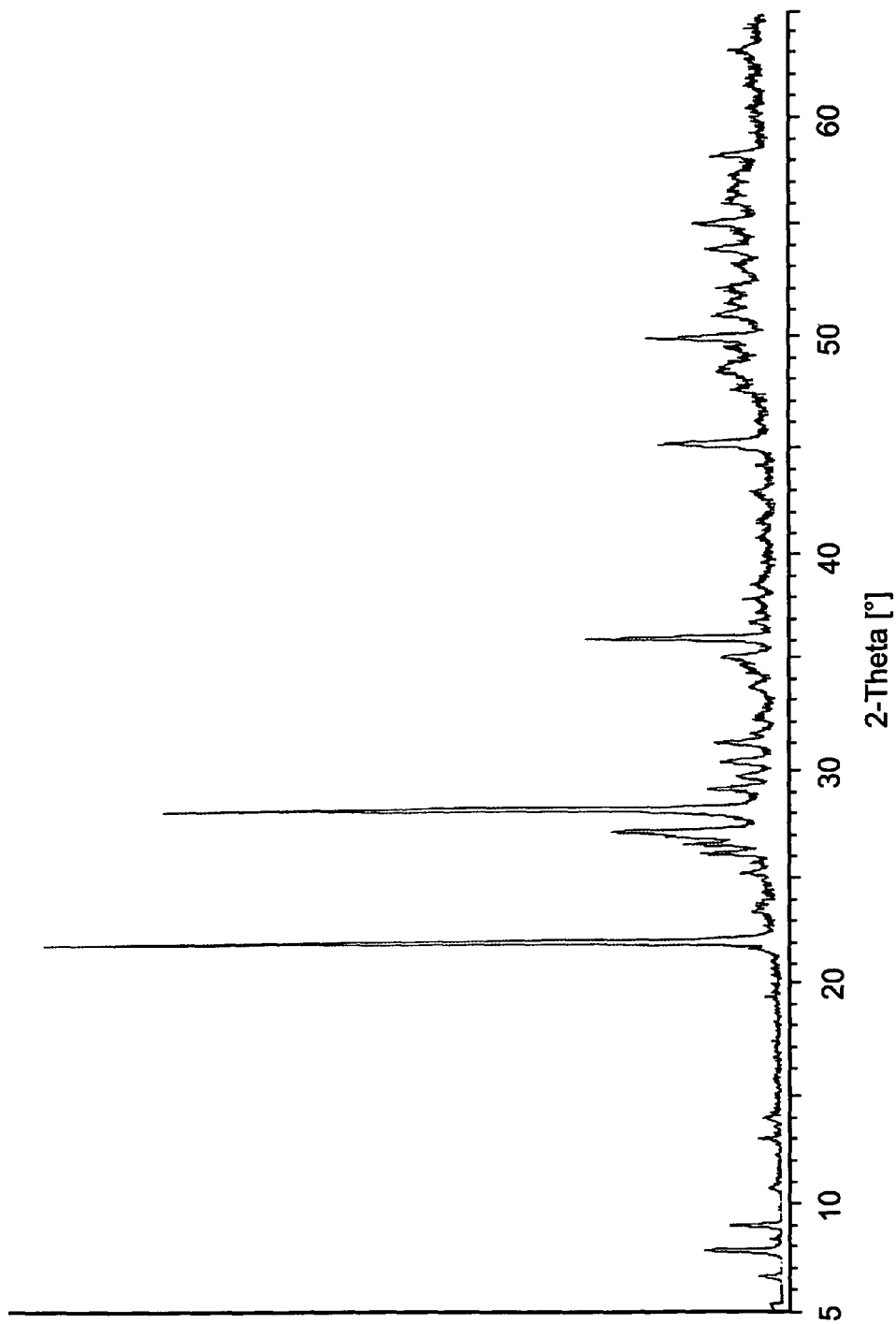
FIG. 12 X-ray diffraction pattern of Comparative Example 6

The resulting active material had the composition $Mo_{1.0}V_{0.33}Te_{0.19}Nb_{0.11}Bi_{0.004}O_x$. The associated X-ray diffraction pattern is shown in FIG. 12 (R=0.18). BET=9.0 m²/g. It was applied in the same manner to the same support as in comparative example 1, so that a coated catalyst VB6 comprising 20% by weight of active material resulted.

Example 6

Figure 13:
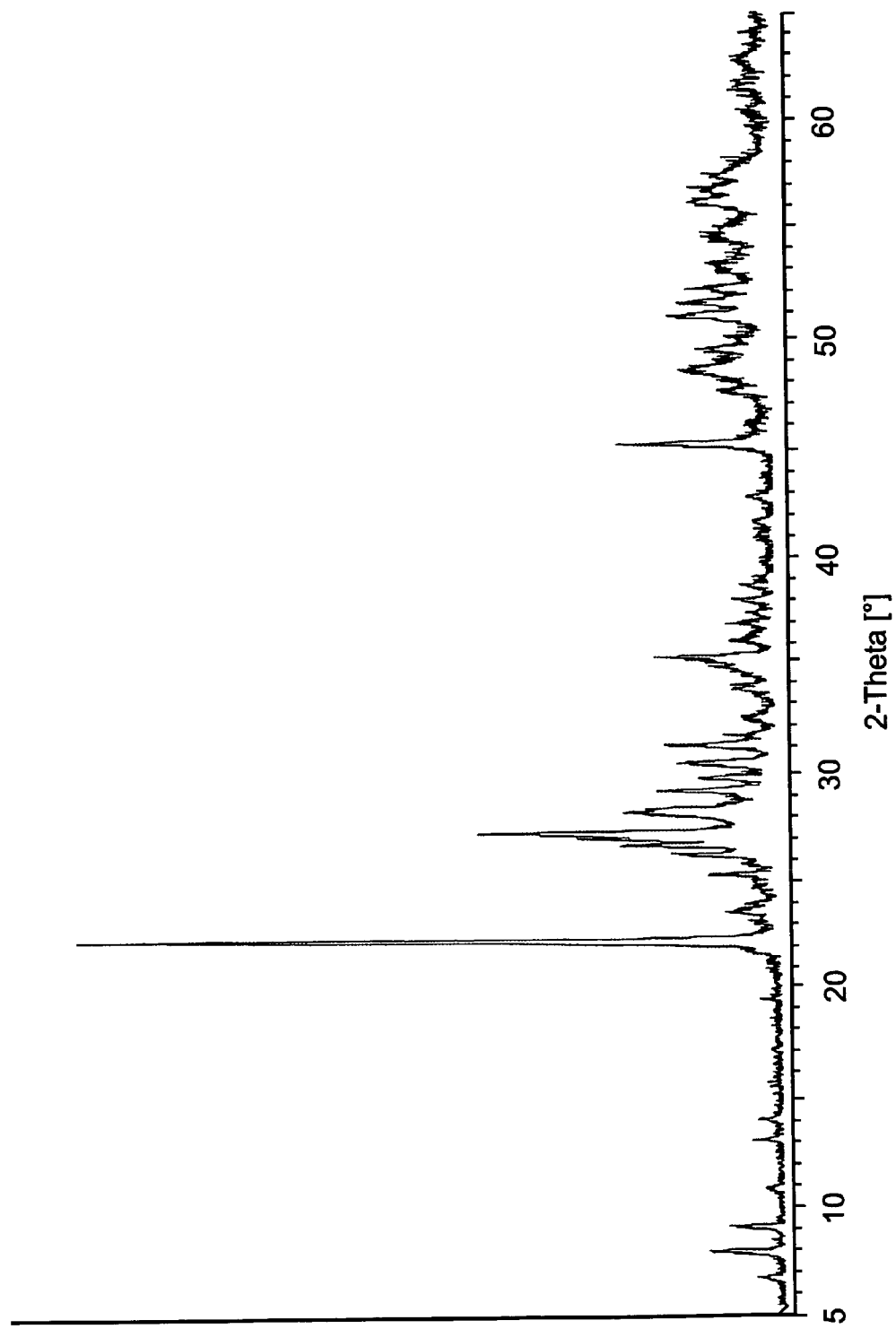
FIG. 13 X-ray diffraction pattern of Example 6

As in example 1, but the active material from comparative example 6 was washed with aqueous nitric acid. The resulting active material had the composition $Mo_{1.0}V_{0.28}Te_{0.15}Nb_{0.14}Bi_{0.005}O_x$. The associated X-ray diffraction pattern is shown in FIG. 13 (R=0.70). BET=22.0 m²/g. It was applied in the same manner to the same support as in comparative example 1, so that the coated catalyst B6 comprising 20% by weight of active material resulted.

Comparative Example 7

As in comparative example 1, but 3.84 g of lead(II) nitrate (Riedel-de-Haen, 99%) were used instead of 6.80 g of nickel(II) nitrate hexahydrate.

Figure 14:
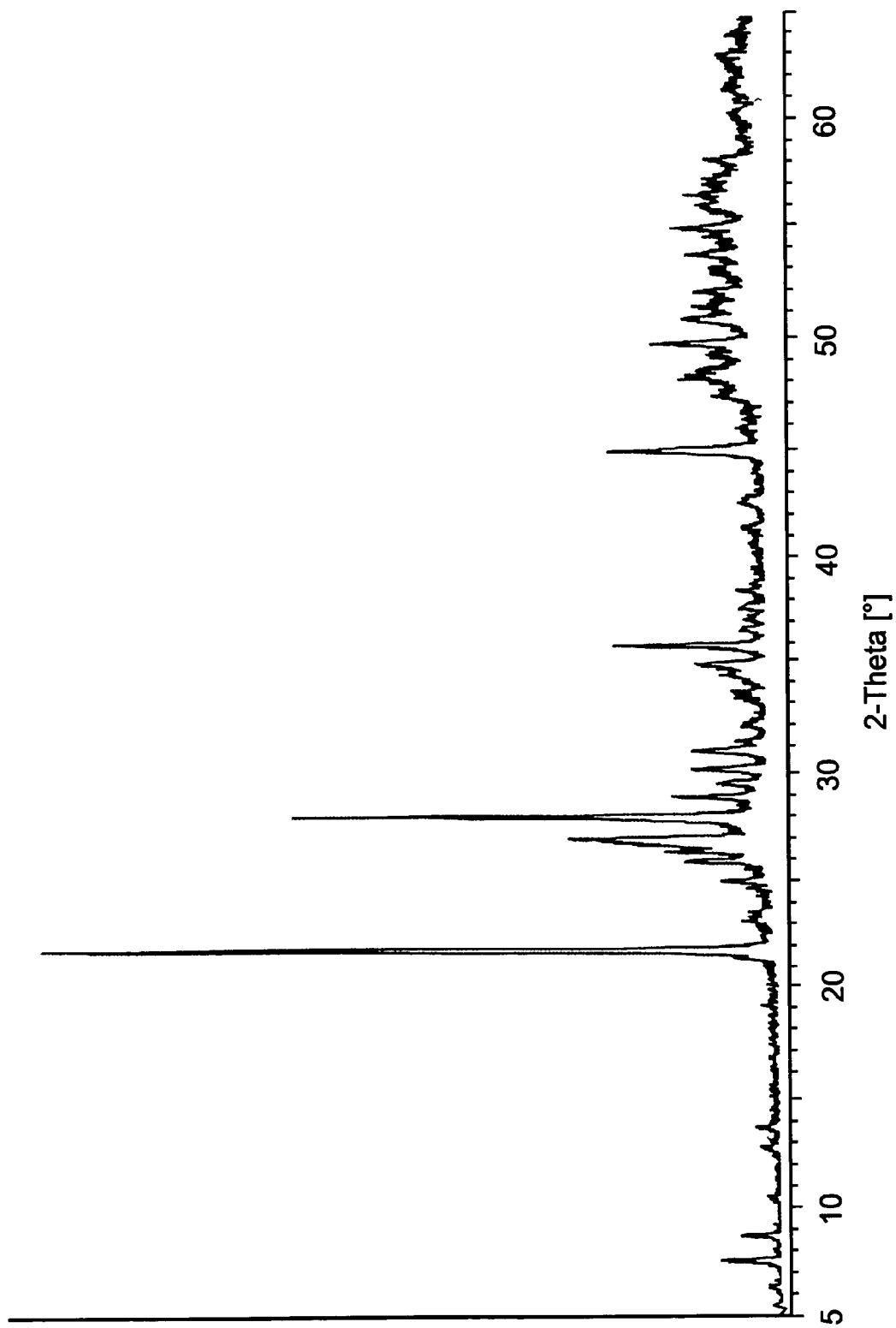
FIG. 14 X-ray diffraction pattern of Comparative Example 7

The resulting active material had the composition $Mo_{1.0}V_{0.29}Te_{0.13}Nb_{0.13}Pb_{0.004}O_x$. The associated X-ray diffraction pattern is shown in FIG. 14 (R=0.30). BET=2.2 m²/g. It was applied in the same manner to the same support as in comparative example 1, so that a coated catalyst VB7 comprising 20% by weight of active material resulted.

Example 7

As in example 1, but the active material from comparative example 7 was washed with aqueous nitric acid. The resulting active material had the composition $Mo_{1.0}V_{0.28}Te_{0.13}Nb_{0.13}Pb_{0.001}O_x$.

Figure 15:
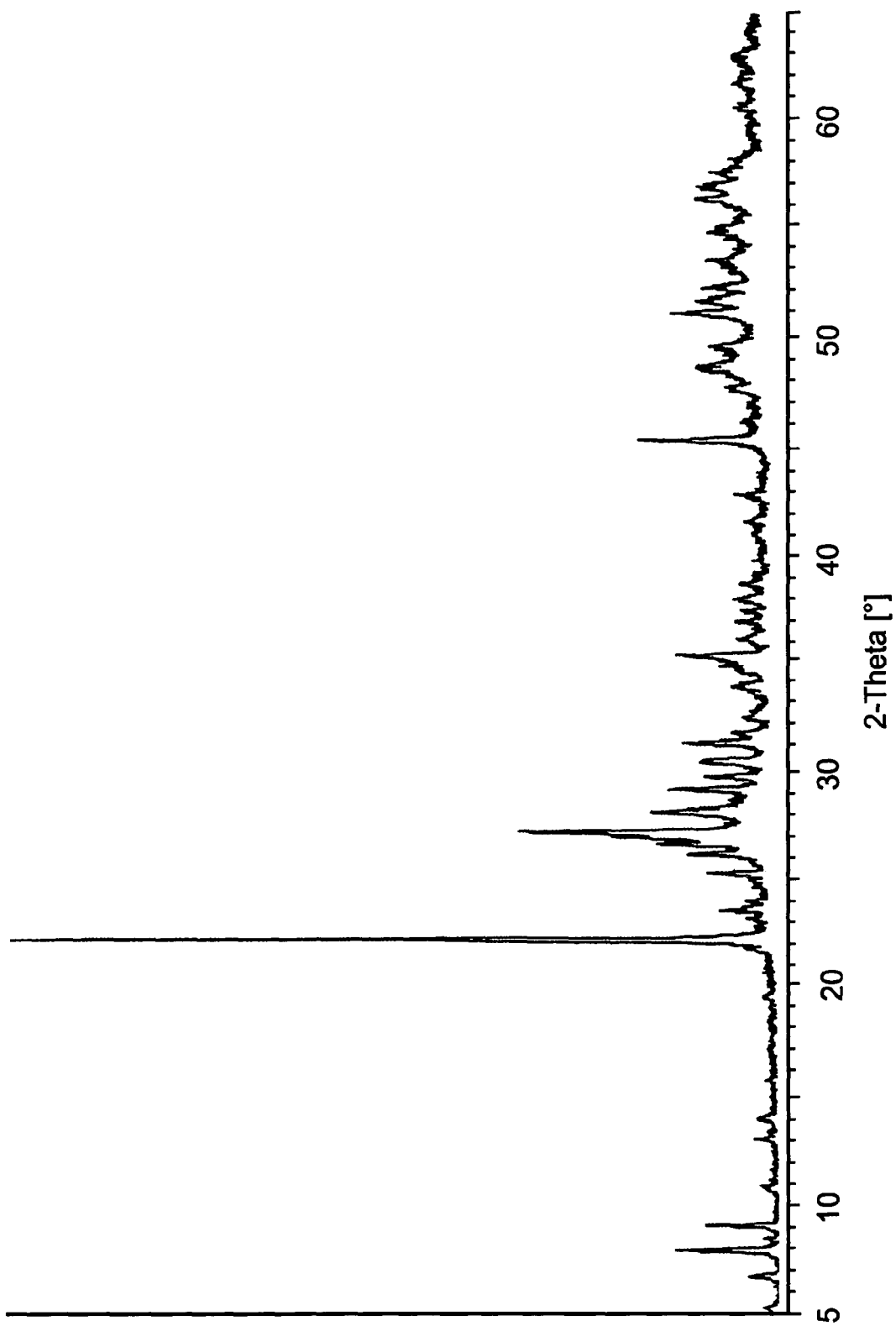
FIG. 15 X-ray diffraction pattern of Example 7

The associated X-ray diffraction pattern is shown in FIG. 15 (R=0.67). BET=27.1 m²/g. It was applied in the same manner to the same support as in comparative example 1, so that a coated catalyst B7 comprising 20% by weight of active material resulted.

Comparative Example 8

Figure 16:
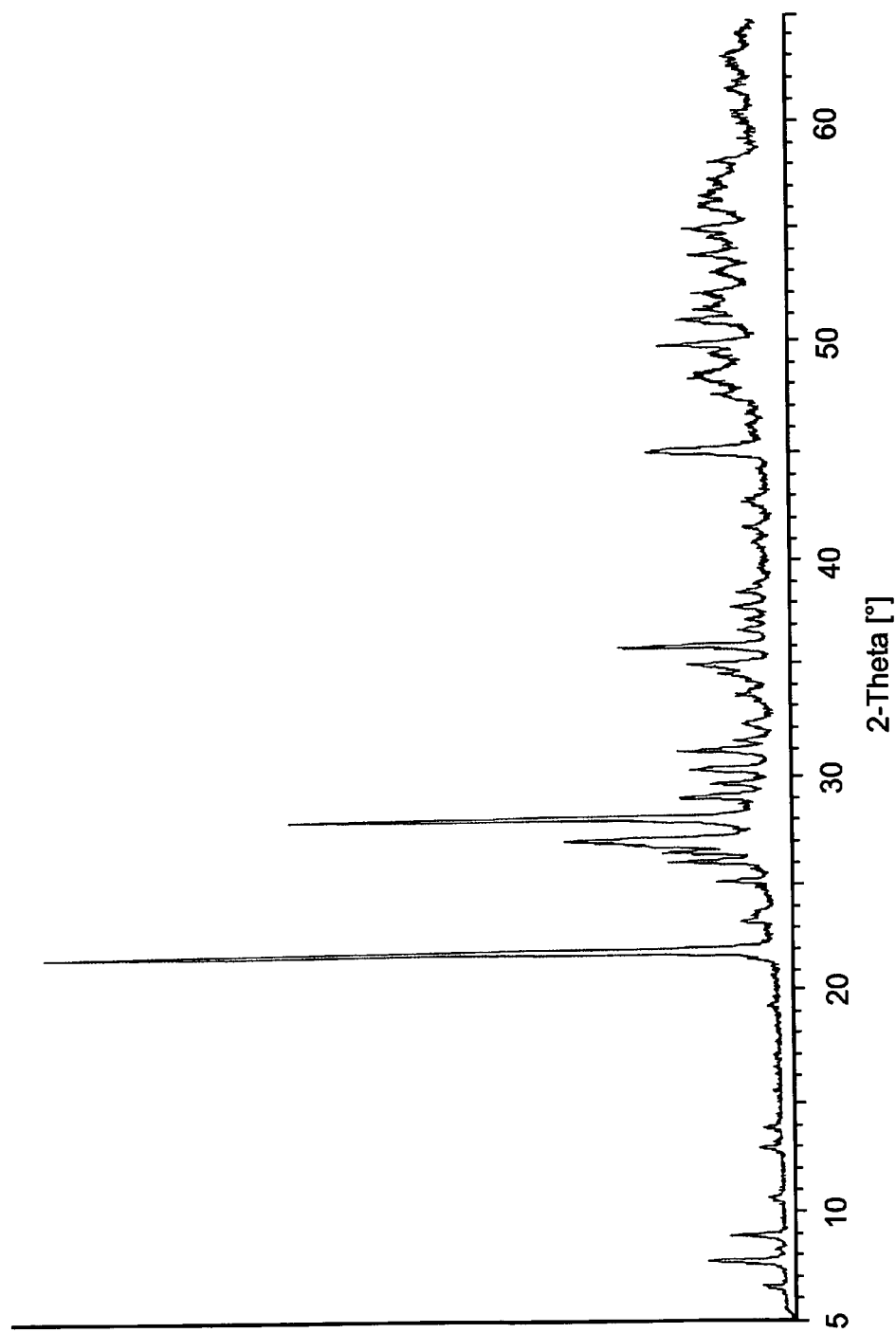
FIG. 16 X-ray diffraction pattern of Comparative Example 8

As in comparative example 1, except that the addition of the 5.60 g of nickel(II) nitrate hexahydrate was not carried out. The resulting active material had the composition $Mo_{1.0}V_{0.33}Te_{0.16}Nb_{0.11}O_x$. The associated X-ray diffraction pattern is shown in FIG. 16 (R=0.26). BET=6.7 m²/g. It was applied in the same manner to the same support as in comparative example 1, so that a coated catalyst VB8 comprising 20% by weight of active material resulted.

Comparative Example 9

As in example 1, but the active material from comparative example 8 was washed with aqueous nitric acid. The resulting active material had the composition $Mo_{1.0}V_{0.29}Te_{0.13}Nb_{0.13}O_x$.

Figure 17:
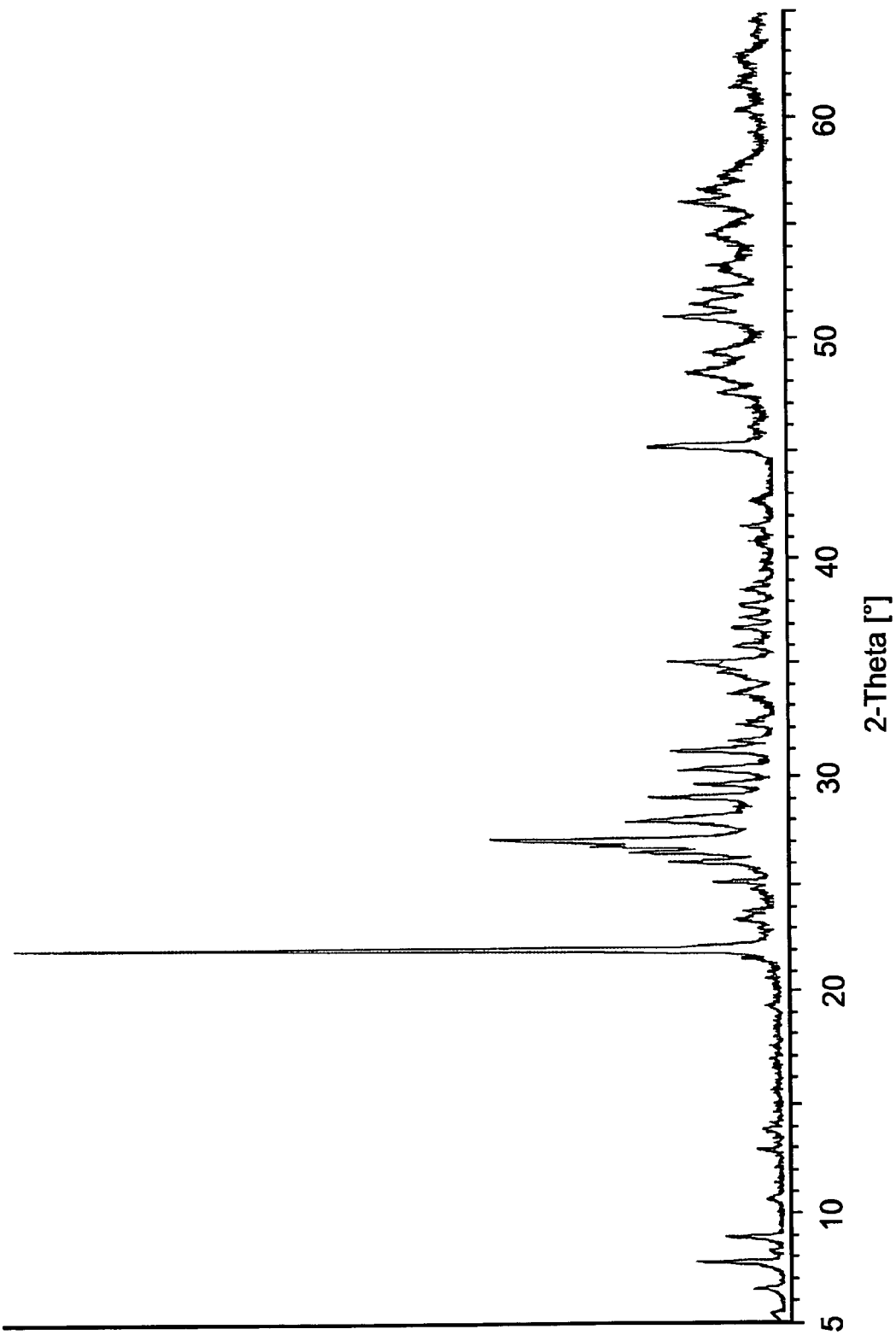
FIG. 17 X-ray diffraction pattern of Comparative Example 9

The associated X-ray diffraction pattern is shown in FIG. 17 (R=0.68). BET=26.0 m²/g. It was applied in the same manner to the same support as in comparative example 1, so that a coated catalyst VB9 comprising 20% by weight of active material resulted.

B) Testing of the Coated Catalyst Prepared in A) and Comprising Multimetal Oxide Materials A tubular reactor made of steel (internal diameter,: 8.5 mm, length: 140 cm, wall thickness: 2.5 cm) was loaded with in each case 35.0 g of the respective coated catalyst from A) (catalyst bed length in all cases about 53 cm). A preliminary bed of 30 cm of steatite beads (diameter: from 2.2 to 3.2 mm, manufacturer: Ceramtec) was installed before the catalyst bed and a subsequent bed of the same steatite beads was installed after the catalyst bed, of the remaining length of the tubular reactor.

The external temperature of the loaded reaction tube was brought to 350° C. over the total length from the outside by means of electrically heated heating mats.

The reaction tube was then fed with a reaction gas starting mixture having the molar composition

| | |
|---|---|
| 5.5% by volume | of acrolein, |
| 0.3% by volume | of propene, |
| 6.0% by volume | of molecular oxygen, |
| 0.4% by volume | of CO, |
| 0.8% by volume | of $CO_2$, |
| 9.0% by volume | of water and |
| 78.0% by volume | of molecular nitrogen |

(the entry side was on the side of the subsequent bed). The residence time (based on the catalyst bed volume) was established at 2.4 seconds. The entry pressure was 2 bar absolute.

The reaction tube load was initially operated over a period of 24 hours in each case at the abovementioned external temperature of the loaded reaction tube, before this external temperature was increased so that an acrolein conversion ($C_{ACR}$) of about 98 mol % based on a single pass through the reaction tube, resulted in all cases.

The table below shows, as a function of the coated catalyst used, the external temperature T (° C.) required for this conversion and the resulting selectivity of the acrylic acid formation ($S_{ACA}$(mol %)). In addition, the table shows the intensity ratio R of the active material present on the coated catalyst and the composition of this active material.

TABLE

| Example | Composition | R | T [° C.] | $C_{ACR}$ (mol %) | $S_{ACA}$ (mol %) |
|---|---|---|---|---|---|
| VB1 | $Mo_1V_{0.33}Te_{0.22}Nb_{0.11}Ni_{0.01}$ | 0.26 | 266 | 98.2 | 91.2 |
| B1 | $Mo_1V_{0.29}Te_{0.14}Nb_{0.13}Ni_{0.007}$ | 0.71 | 258 | 99.3 | 95.5 |
| VB2 | $Mo_1V_{0.33}Te_{0.19}Nb_{0.11}Pd_{0.01}$ | 0.25 | 269 | 98.1 | 90.6 |
| B2 | $Mo_1V_{0.28}Te_{0.13}Nb_{0.13}Pd_{0.001}$ | 0.73 | 251 | 99.2 | 95.1 |
| VB3 | $Mo_1V_{0.33}Te_{0.22}Nb_{0.11}Pd_{0.04}$ | 0.35 | 267 | 98 | 90.3 |
| B3 | $Mo_1V_{0.29}Te_{0.13}Nb_{0.13}Pd_{0.001}$ | 0.74 | 253 | 99.3 | 95.6 |
| VB4 | $Mo_1V_{0.33}Te_{0.19}Nb_{0.11}Co_{0.005}$ | 0.24 | 263 | 97.6 | 91 |
| B4 | $Mo_1V_{0.29}Te_{0.13}Nb_{0.13}Co_{0.004}$ | 0.73 | 259 | 99.3 | 95.1 |
| VB5 | $Mo_1V_{0.33}Te_{0.19}Nb_{0.11}Cu_{0.01}$ | 0.27 | 281 | 98.1 | 89.6 |
| B5 | $Mo_1V_{0.28}Te_{0.13}Nb_{0.13}Cu_{0.003}$ | 0.74 | 262 | 99.3 | 93.9 |
| VB6 | $Mo_1V_{0.33}Te_{0.19}Nb_{0.11}Bi_{0.004}$ | 0.18 | 283 | 98.2 | 88.5 |
| B6 | $Mo_1V_{0.28}Te_{0.15}Nb_{0.14}Bi_{0.005}$ | 0.70 | 261 | 99.3 | 94.6 |
| VB7 | $Mo_1V_{0.34}Te_{0.18}Nb_{0.11}Pb_{0.004}$ | 0.30 | 269 | 98.8 | 90.2 |
| B7 | $Mo_1V_{0.28}Te_{0.13}Nb_{0.13}Pb_{0.001}$ | 0.67 | 257 | 99.3 | 94.1 |
| VB8 | $Mo_1V_{0.33}Te_{0.16}Nb_{0.11}$ | 0.26 | 278 | 96 | 88 |
| VB9 | $Mo_1V_{0.29}Te_{0.13}Nb_{0.13}$ | 0.68 | 263 | 99.3 | 91.9 |

We claim:

1. A process for the heterogeneously catalyzed gas-phase partial oxidation of acrolein to acrylic acid over a catalytically active multimetal oxide material which contains the elements Mo and V, at least one of the elements Te and Sb and at least one of the elements from the group consisting of Nb, Ta, W, Ce and Ti and whose X-ray diffraction pattern has no reflections with the peak position 2θ=50.0±0.3° but has reflections h, i and k whose peaks are at the diffraction angles (2θ) 22.2±0.5° (h), 27.3±0.5° (i) and 28.2±0.5° (k),
the reflection h being the one with the strongest intensity within the X-ray diffraction pattern and having a full width at half height of not more than 0.5°,
the intensity $P_i$ of the reflection i and the intensity $P_k$ of the reflection k fulfilling the relationship 0.65≦R≦0.85, where R is the intensity ratio defined by the formula $$R=P_i/(P_i+P_k)$$

and
the full width at half height of the reflection i and of the reflection k being in each case ≦1°,
wherein the catalytically active multimetal oxide material is one of the stoichiometry (I)

$$Mo_1V_aM^1_bM^2_cM^3_dO_n \quad (I),$$

where
$M^1$ is at least one of the elements from the group consisting of Te and Sb;
$M^2$ is at least one of the elements from the group consisting of Nb, Ti, W, Ta and Ce;
$M^3$ is at least one of the elements from the group consisting of Pb, Ni, Co, Bi, Pd, Ag, Pt, Cu, Au, Ga, Zn, Sn, In, Re, Ir, Sm, Sc, Y, Pr, Nd and Tb;
a=from 0.01 to 1,
b=from >0 to 1,
c=from >0 to 1,
d=from >0 to 0.5 and
n is a number which is determined by the valency and frequency of the elements other than oxygen in (I).

2. The process as claimed in claim 1, wherein 0.67≦R≦0.75.

3. The process as claimed in claim 1, wherein 0.69≦R≦0.75.

4. The process as claimed in claim 1, wherein 0.71≦R≦0.74.

5. The process as claimed in claim 1, wherein R=0.72.

6. The process as claimed in any of claims 1 to 5, wherein the specific surface area of the catalytically active multimetal oxide material (I) is from 11 to 40 m²/g.

7. The process as claimed in claim 1, wherein the X-ray diffraction pattern of the catalytically active multimetal oxide material (I) has further reflections having their peak position at the following diffraction angles 2θ:
9.0±0.4° (l),
6.7±0.4° (o) and
7.9±0.4° (p).

8. The process as claimed in claim 7, wherein the X-ray diffraction pattern of the catalytically active multimetal oxide material (I) has further reflections with their peak position at the following diffraction angles 2θ:
29.2±0.4° (m) and
35.4±0.4° (n).

9. The process as claimed in claim 8, wherein the reflections h, i, l, m, n, o, p and q have the following intensities on the same intensity scale:
h=100,
i=from 5 to 95,
l=from 1 to 30,
m=from 1 to 40,
n=from 1 to 40,
o=from 1 to 30,
p=from 1 to 30 and
q=from 5 to 60.

10. The process as claimed in claim 1, wherein a=from 0.05 to 0.6.

11. The process as claimed in claim 1, wherein b=from 0.01 to 1.

12. The process as claimed in claim 1, wherein c=from 0.01 to 1.

13. The process as claimed in claim 1, wherein d=from 0.0005 to 0.5.

14. The process as claimed in claim 1, wherein
a=from 0.1 to 0.6,
b=from 0.1 to 0.5,
c=from 0.1 to 0.5 and
d=from 0.001 to 0.5.

15. The process as claimed in claim 1, wherein at least 50 mol % of $M^2$, based on its total amount, is Nb.

16. The process as claimed in claim 1, wherein at least 75 mol % of $M^2$, based on its total amount, is Nb.

17. The process as claimed in claim 1, wherein $M^2$ is exclusively Nb.

18. The process as claimed in claim 1, wherein $M^3$ is at least one element from the group consisting of Ni, Co, Bi, Pd, Ag, Au, Pb and Ga.

19. The process as claimed in claim 1, wherein $M^3$ is at least one element from the group consisting of Ni, Co, Pd and Bi.

20. The process as claimed in claim 1, wherein $M^1$ is Te, $M^2$ is Nb and $M^3$ is at least one element from the group consisting of Ni, Co and Pd.

21. The process as claimed in claim 1, wherein the multimetal oxide material (I) is contained in a total multimetal oxide material whose X-ray diffraction pattern has no reflection with the peak position $2\theta=50.0\pm0.3°$.

22. The process as claimed in claim 21, wherein the multimetal oxide material (I) is present in the total multimetal oxide material in a form diluted with at least one finely divided material from the group consisting of silica, titanium dioxide, alumina, zirconium oxide and niobium oxide.

23. The process as claimed in claim 22, wherein the total multimetal oxide material contains $\geq 80\%$ by weight of multimetal oxide material (I) and the X-ray diffraction pattern of the total multimetal oxide material has a reflection with the peak position $2\theta=50.0\pm0.3°$.

24. The process as claimed in claim 22, wherein $R \geq 0.65$ and $\leq 0.90$ is fulfilled for the X-ray diffraction pattern of the total multimetal oxide material.

25. The process as claimed in claim 1, wherein the heterogeneously catalyzed gas-phase partial oxidation of acrolein is effected in the presence of propane and/or propene.

26. The process as claimed in claim 1, which is carried out in a tube-bundle reactor.

27. The process as claimed in claim 1, wherein the catalytically active multimetal oxide material (I) is a component of a coated catalyst.

* * * * *